(12) United States Patent
Lim

(10) Patent No.: US 8,718,775 B2
(45) Date of Patent: May 6, 2014

(54) IMPLANTABLE PULSE GENERATOR EMI FILTERED FEEDTHRU

(75) Inventor: Wisit Lim, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 1101 days.

(21) Appl. No.: 12/715,301

(22) Filed: Mar. 1, 2010

(65) Prior Publication Data

US 2010/0160991 A1   Jun. 24, 2010

Related U.S. Application Data

(63) Continuation-in-part of application No. 12/425,675, filed on Apr. 17, 2009, now Pat. No. 8,391,983, and a continuation-in-part of application No. 12/117,090, filed on May 8, 2008.

(51) Int. Cl.
*A61N 1/362* (2006.01)

(52) U.S. Cl.
USPC .................................. 607/37; 607/9; 607/36

(58) Field of Classification Search
USPC ...................................................... 607/36–37
See application file for complete search history.

(56) References Cited

U.S. PATENT DOCUMENTS

| 5,896,267 | A | * | 4/1999 | Hittman et al. | 361/302 |
|---|---|---|---|---|---|
| 5,959,829 | A | * | 9/1999 | Stevenson et al. | 361/302 |
| 6,052,623 | A | * | 4/2000 | Fenner et al. | 607/36 |
| 6,424,234 | B1 | | 7/2002 | Stevenson | |
| 6,778,040 | B2 | * | 8/2004 | Kim | 333/182 |
| 2007/0203529 | A1 | * | 8/2007 | Iyer et al. | 607/37 |
| 2007/0203530 | A1 | * | 8/2007 | Hubing et al. | 607/37 |

* cited by examiner

*Primary Examiner* — Carl H Layno
*Assistant Examiner* — Jennifer Ghand

(57) ABSTRACT

An implantable pulse generator includes a header, a can and a feedthru. The feedthru is mounted in a wall of the can and includes an electrically insulating core, a PCB, a shield, a chip capacitor, a power circuit and a ground circuit. A first side of the PCB abuts against the core and a second side of the PCB abuts against an edge of the shield. The chip capacitor is mounted on the second side of the PCB. The chip capacitor is enclosed in a volume defined by an interior of the shield and the second side of the PCB. A first electrical contact of the chip capacitor is electrically coupled to the power circuit, and a second electrical contact of the chip capacitor is electrically coupled to the ground circuit.

13 Claims, 29 Drawing Sheets

IMPLANTABLE PULSE GENERATOR EMI FILTERED FEEDTHRU

CROSS-REFERENCE TO RELATED APPLICATIONS

The present application is a continuation-in-part ("CIP") of U.S. patent application Ser. No. 12/425,675, now U.S. Pat. No. 8,391,983, filed Apr. 17, 2009 and is a CIP of copending U.S. patent application Ser. No. 12/117,090, filed May 8, 2008. Each of these applications is hereby incorporated by reference in their entireties into the present application.

FIELD OF THE INVENTION

The present invention relates to medical apparatus and methods. More specifically, the present invention relates to feedthrus for implantable pulse generators and methods of manufacturing such feedthrus.

BACKGROUND OF THE INVENTION

Implantable pulse generators, such as pacemakers, defibrillators or implantable cardioverter defibrillators ("ICD"), are used to provide electrotherapy to cardiac tissue via implantable medical leads. An implantable pulse generator feedthru is used for an electrical pathway extending between the electrically conductive lead securing components of a header of the pulse generator and the electrical components, such as an output flex, hybrid, etc., hermetically sealed in the housing or can of the pulse generator.

Feedthrus are mounted in the wall of the housing or can and include feedthru wires extending through the feedthrus. Feedthrus provide insulated passageways for feedthru wires, such as platinum iridium (Pt/Ir) wires, through the wall of the can. The header ends of the feedthru wires are electrically connected to connector blocks that mechanically and electrically couple with connector ends of implantable medical leads, and the can ends of the feedthru wires are electrically connected to the electrical components housed in the can of the pulse generator.

There are a number of disadvantages associated with current feedthru designs. For example, current feedthrus employ discoidal filter assemblies for filtering out unwanted signals, such as those associated with electro-magnetic interference ("EMI"). Discoidal filter assemblies have high associated material and manufacturing costs.

There is a need in the art for a feedthru that has reduced material and manufacturing costs. Also, there is a need in the art for a method of manufacturing such a feedthru.

BRIEF SUMMARY OF THE INVENTION

Disclosed herein is an implantable pulse generator. In one embodiment, the implantable pulse generator includes a header, a can and a feedthru. The header may include a lead connector block electrically coupled to a first conductor. The can may be coupled to the header and include a wall and an electronic component electrically coupled to a second conductor and housed within the wall. The feedthru may be mounted in the wall and include a header side with a first electrically conductive tab and a can side with a second electrically conductive tab electrically coupled to the first tab. The first tab is electrically coupled to the first conductor and the second tab is electrically coupled to the second conductor. In one embodiment, a chip capacitor may be located on a can side of the feedthru.

Disclosed herein is an implantable pulse generator feedthru. In one embodiment, the feedthru includes: an electrically insulating body including a header side and a can side; a ground circuit at least a portion of which is on the body; and a power circuit including a first tab on one of the sides. In one embodiment, the feedthru may further include a chip capacitor coupled to the body and including a power side electrically coupled to the power circuit and a ground side electrically coupled to the ground circuit.

Disclosed herein is an implantable pulse generator feedthru. In one embodiment, the feedthru includes: an electrically insulating body including a header side and a can side; a ground side conductive path operably coupled to the body; and a power side conductive path extending through the body, wherein the conductive path is not a feedthru wire. In one embodiment, the feedthru further includes a chip capacitor coupled to the body and including a power side electrically coupled to the power side conductive path and a ground side electrically coupled to the ground side conductive path.

Disclosed herein is an implantable pulse generator. In one embodiment, the pulse generator includes a header, a can, a feedthru, and a chip capacitor. The header may include a lead connector block electrically coupled to a first conductor. The can may be coupled to the header and include a wall and an electronic component electrically connected to a second conductor and housed within the wall. The feedthru may be mounted in the wall and comprises an electrically insulating core and a power circuit. The chip capacitor may be mounted on the feedthru. The core may include a first side, a second side generally opposite the first side, and a third side generally lateral the second side. The power circuit may extend between the three sides. The first conductor may be electrically connected to the power circuit at the first side. The second conductor may be electrically connected to the power circuit at the third side. The power side of the chip capacitor may be electrically connected to the power circuit at the second side.

Also disclosed herein is yet another implantable pulse generator. In one embodiment, the pulse generator includes a header, a can, and a feedthru. The header includes a lead connector block electrically coupled to a first conductor. The can is coupled to the header and includes a wall and an electronic component electrically coupled to a second conductor and housed within the wall. The feedthru is mounted in the wall and includes a header side, a can side, an electrical insulating core, a PCB, a chip capacitor, a ground circuit, and a power circuit. The core includes a first surface and a second surface, the first surface of the core forming at least part of the header side. The PCB includes a first surface and a second surface. The first surface of the PCB abuts against the second surface of the core. The second surface of the PCB forms at least part of the can side and includes a first electrically conductive region, a second electrically conductive region, and a first electrically non-conductive region separating the first electrically conductive region from the second electrically conductive region. The power circuit extends through the PCB and core from the second conductor to the first conductor and is electrically connected to the second electrically conductive region. In one embodiment, the power circuit extending through the PCB and core may include a wire. The chip capacitor includes a first electrical contact electrically connected to the first electrically conductive region and a second electrical contact electrically connected to the second electrically conductive region. The chip capacitor spans across the first electrically non-conductive region. At least a portion of the ground circuit extends along the first electrically conductive region and is electrically coupled to the wall.

Disclosed herein is yet another implantable pulse generator. In one embodiment, the implantable pulse generator includes a header, a can and a feedthru. The header includes a lead connector block electrically coupled to a first conductor. The can is coupled to the header and includes a wall and an electronic component electrically connected to a second conductor and housed within the wall. The feedthru is mounted in the wall and includes an electrically insulating core, a PCB, a shield, a chip capacitor, a power circuit and a ground circuit. A first side of the PCB abuts against the core and a second side of the PCB abuts against an edge of the shield. The chip capacitor is mounted on the second side of the PCB. The chip capacitor is enclosed in a volume defined by an interior of the shield and the second side of the PCB. A first electrical contact of the chip capacitor is electrically coupled to the power circuit, which extends between the first and second conductors. A second electrical contact of the chip capacitor is electrically coupled to the ground circuit, which is electrically coupled to the wall.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Figure 1:
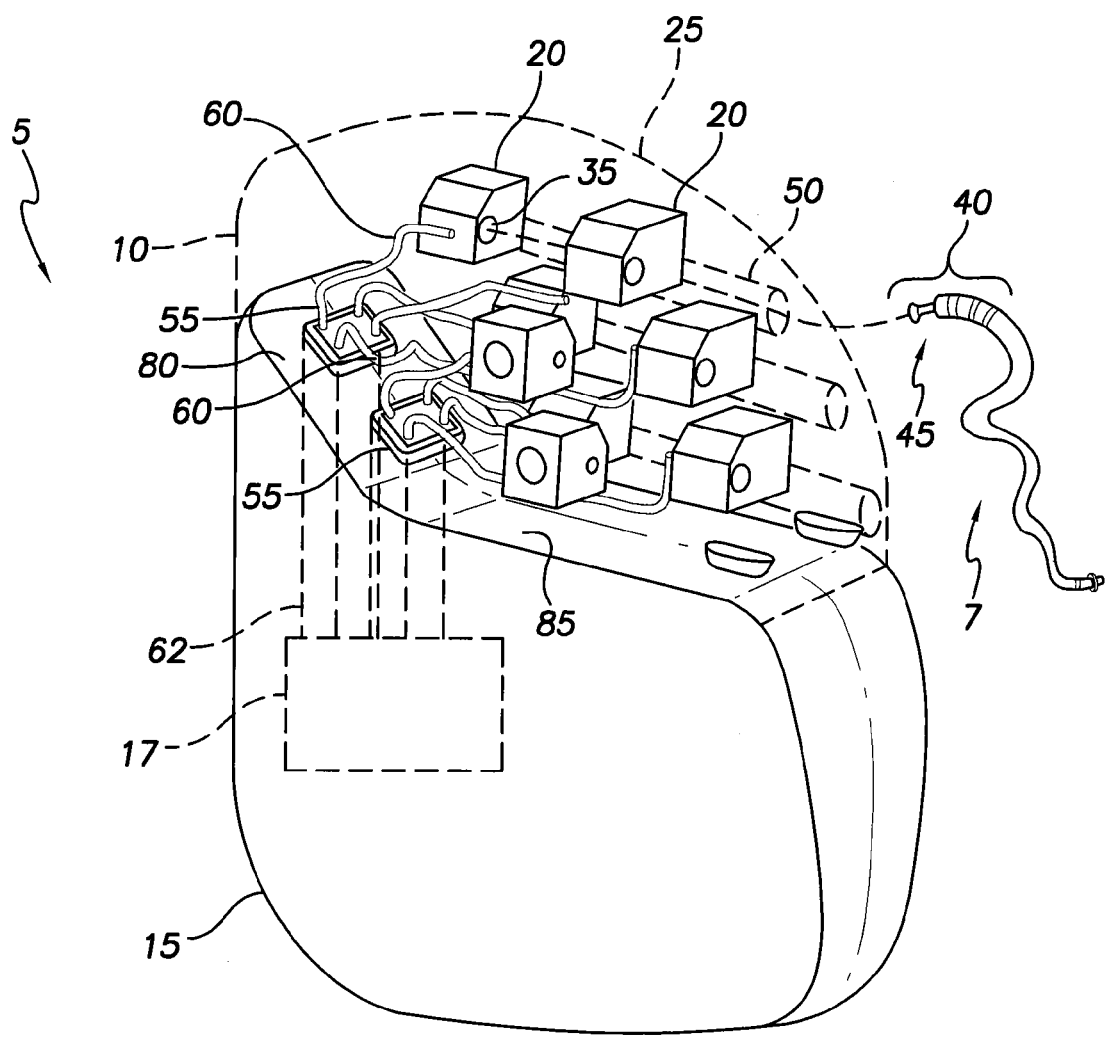
FIG. 1 is an isometric view of an implantable pulse generator employing a feedthru according to the present disclosure.

The present disclosure describes a feedthru 55 of an implantable pulse generator 5 such as a defibrillator, a pacemaker or an ICD. The feedthru 55 disclosed herein includes tabs 70 for electrical communication between the components of the header 10 (e.g., the connector blocks 20) and the electrical components 17 (e.g., output flex, hybrid, etc.) housed within the can 15. The feedthru 55 provides an electrically insulated passageway for electrical communication via the tabs 70 through the can wall 65.

Generally, the tabs 70 and the components 20, 17 of the header 10 and the can 15 are in electrical communication via conductors 60, 62 such as round wire, flat ribbon wire, flex cable, etc. The feedthru 55 reduces manufacturing and material costs because it does not employ feedthru wires, which are typically made of expensive Pt/Ir. The feedthru 55 further reduces material and design costs by utilizing an off-the-shelf chip capacitor 90 as an EMI filter element, the chip capacitor 90 being less expensive than a discoidal capacitor with respect to material and manufacturing costs. Due in part to its lack of feedthru wires, the feedthru 55 is generally compact and low profile and can therefore be installed in the inclined portion 80 and/or the flat portion 85 of the can 15 or any other part of the can 15 including the vertical side walls.

For a general discussion of an implantable pulse generator 5 that utilizes the feedthru 55 disclosed herein, reference is first made to FIG. 1, which is an isometric view of such an implantable pulse generator 5. As indicated in FIG. 1, the pulse generator 5 includes a header 10 and a can or housing 15. The header 10 includes connector blocks 20 and a molded portion 25 (shown in phantom) that encloses the blocks 20. Each block 20 includes an opening 35 configured to receive therein and mate with a connector end 40 of a lead proximal end 45, thereby forming an electrical connection between the connector block 20 and the lead connector end 40 and mechanically securing the proximal end 45 of the lead 7 to the header 10 of the pulse generator 5.

The header molded portion 25 (shown in phantom) may be formed of a polymer material. Passages 50 (shown in phantom) extend from the exterior of the molded portion 25 to the openings 35 in the blocks 20, providing a pathway for the lead distal ends 40 to pass through the molded portion 25 and enter the openings 35.

The can 15 includes feedthrus 55 mounted in the wall of the can 15. Conductors 60 (e.g., round wires, flat ribbon wires, flex cables or etc.) extend from the header sides of the feedthrus 55 to respective connector blocks 20. The can 15 provides a hermetically sealed enclosure for the pulse generator's electronic components 17 (e.g., output flex, hybrid, or various other electronic components) housed within the can 15. Conductors 62 (e.g., round wires, flat ribbon wires, flex cables or etc.) extend from the can sides of the feedthrus 55 to the electronic components 17. Typically, the wall of the can 15 is made of titanium or another biocompatible metal.

As shown in FIG. 1, in one embodiment, the feedthrus 55 are mounted in an inclined portion 80 of the can 15. In other embodiments, the feedthrus 55 may be mounted in a flat portion 85 of the pulse generator 5, or the feedthrus 55 may be mounted in both the inclined and flat portions 80, 85 of the can 15. In yet other embodiments, the feedthrus 55 may be mounted on the vertical side walls of the can 15.

Figure 2A:
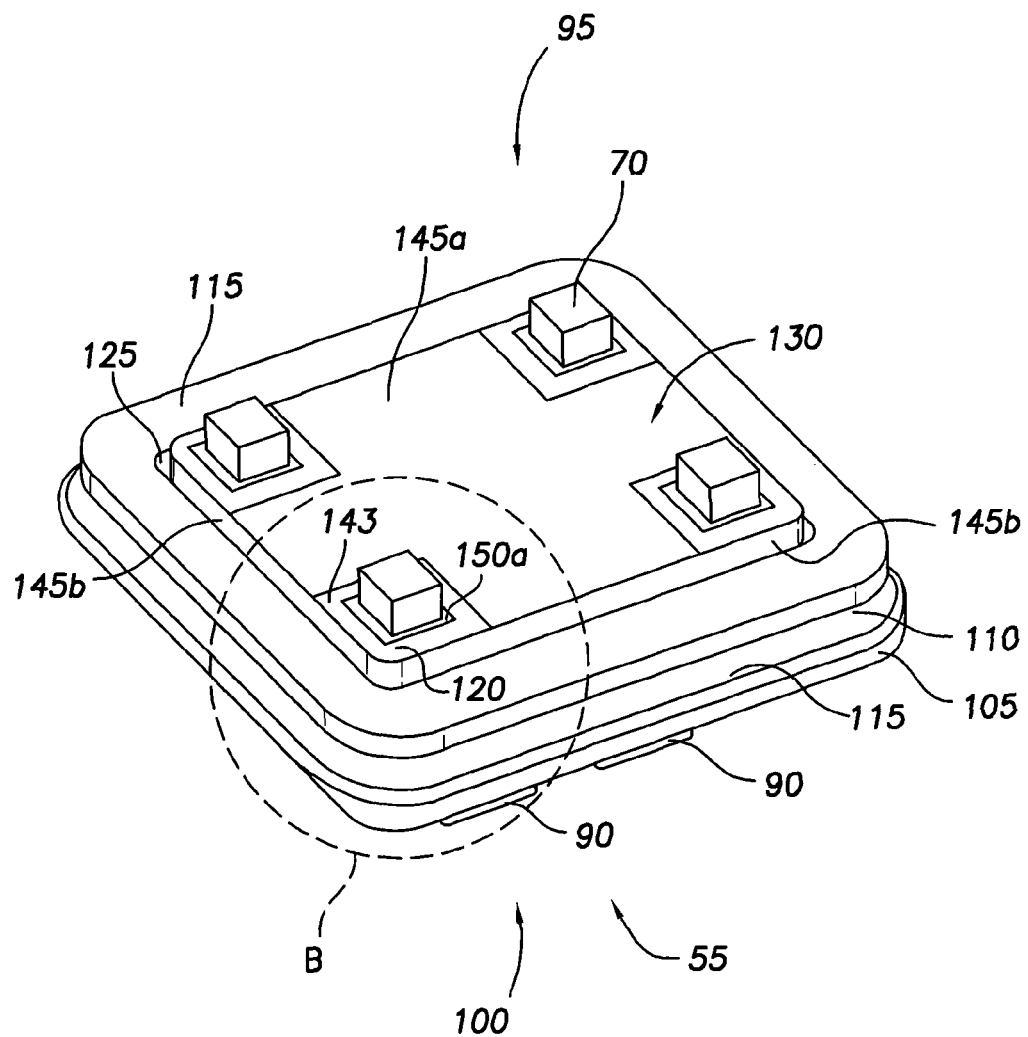
FIG. 2A is a top isometric view of the feedthru of FIG. 1.
Figure 2B:
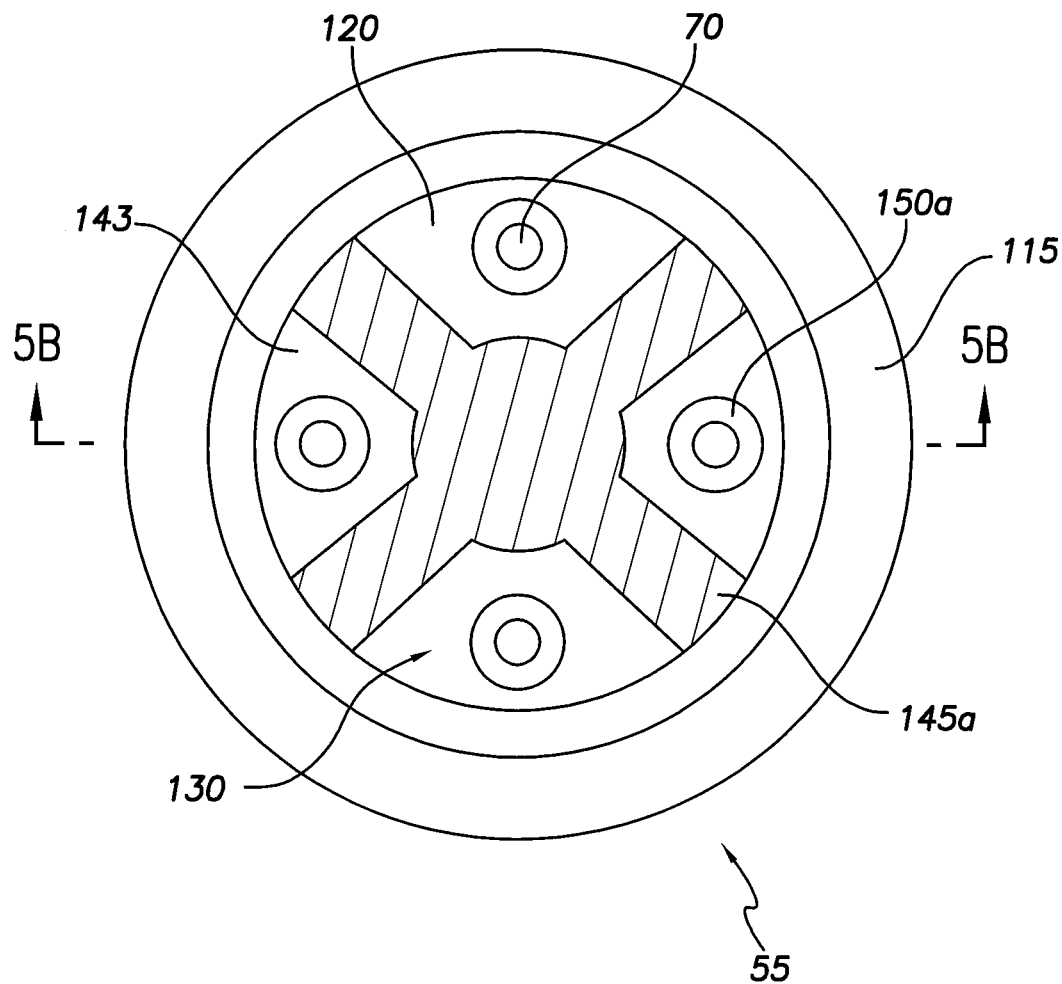
FIG. 2B is a top plan view of an alternative embodiment of the feedthru of FIG. 1.
Figure 3A:
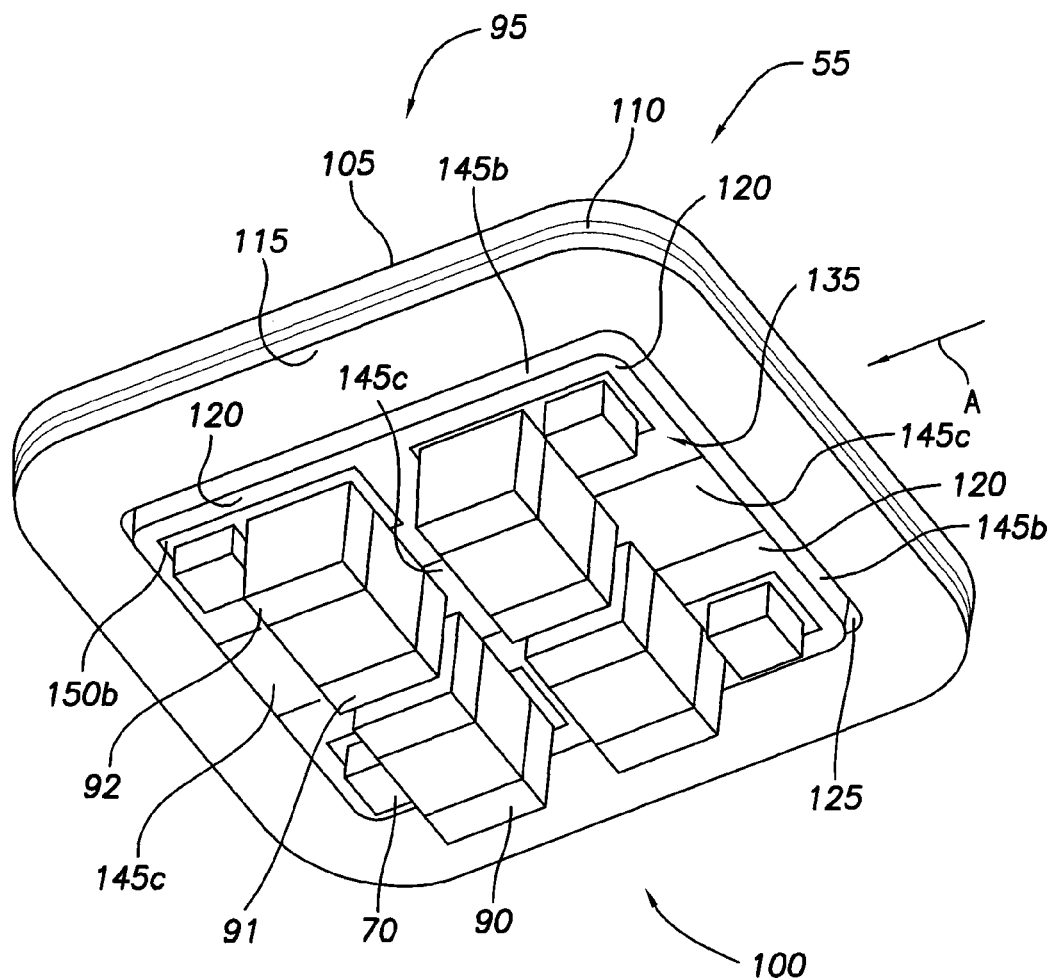
FIG. 3A is a bottom isometric view of the feedthru of FIG. 1.
Figure 3B:
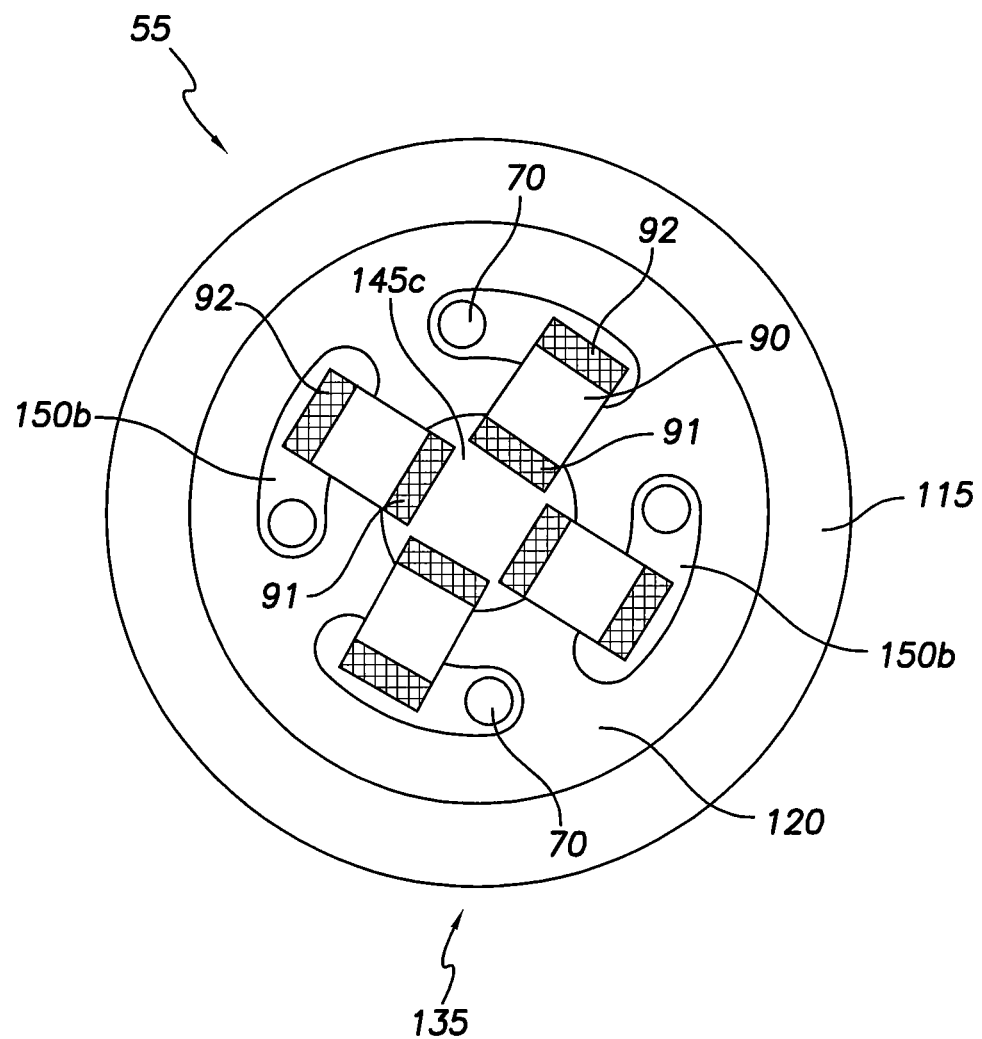
FIG. 3B is a bottom plan view of an alternative embodiment of the feedthru of FIG. 1.
Figure 4:
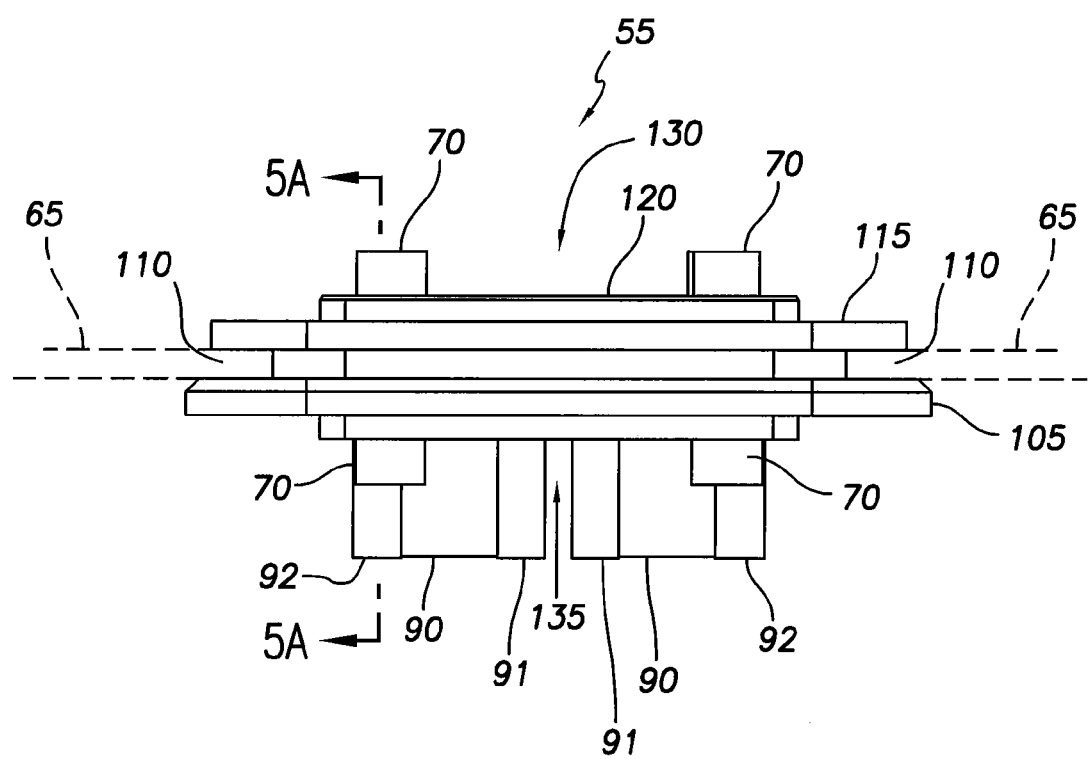
FIG. 4 is a side view of the feedthru taken from the direction of arrow "A" of FIG. 3A.
Figure 5A:
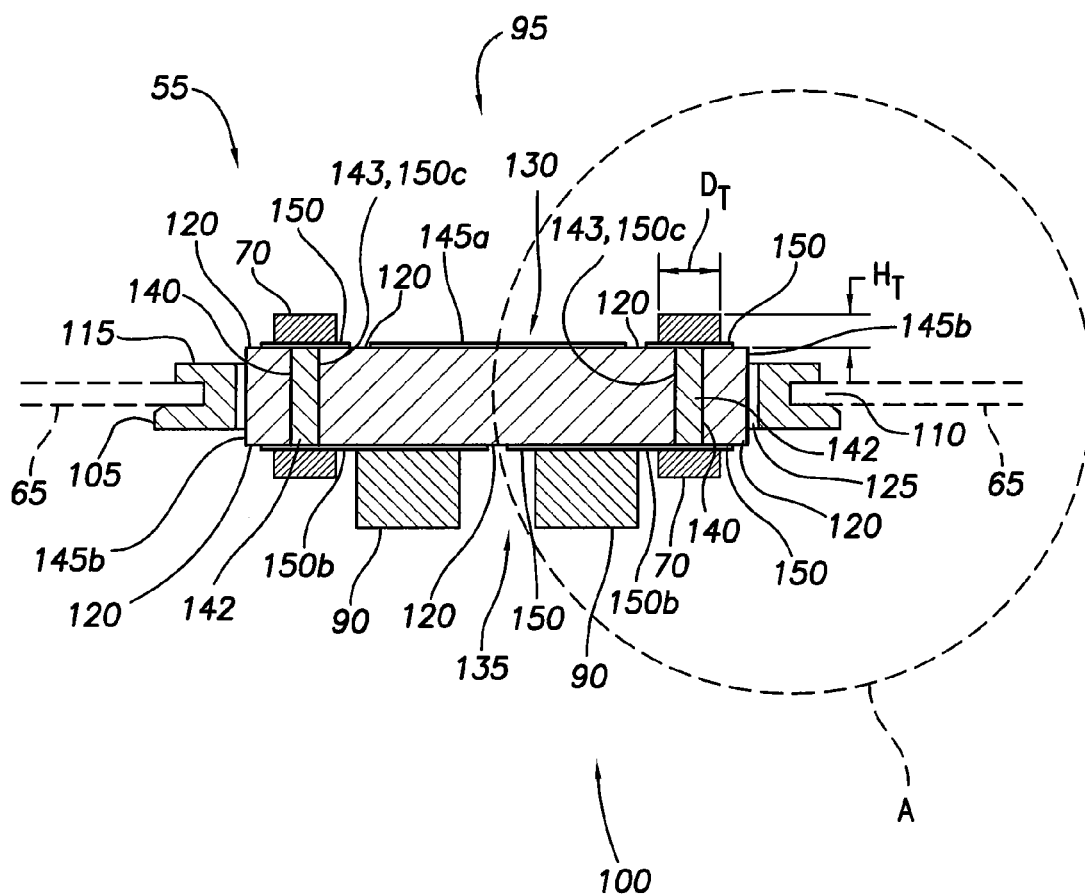
FIG. 5A is a longitudinal cross-sectional elevation of the feedthru as taken along section line 5A-5A of FIG. 4.
Figure 5B:
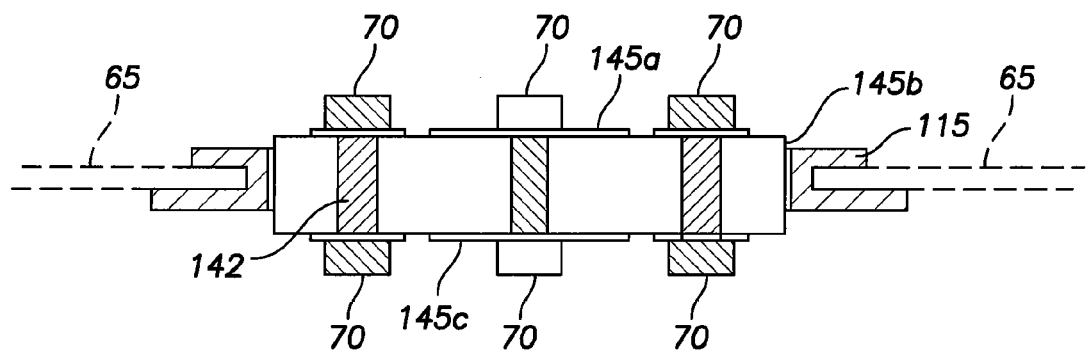
FIG. 5B is a longitudinal cross-sectional elevation of an alternative embodiment of the feedthru as taken along section line 5B-5B of FIG. 2B, wherein the chip capacitors are not shown for clarity purposes.

For a detailed discussion of the components of the feedthru 55, reference is now made to FIGS. 2A-5B. FIG. 2A and FIG. 3A are, respectively, top and bottom isometric views of the feedthru 55 of FIG. 1. FIG. 2B and FIG. 3B are, respectively, top and bottom plan views of an alternative embodiment of the feedthru 55 of FIG. 1. FIG. 4 is a side view of the feedthru 55 taken from the direction of arrow "A" of FIG. 3A. FIG. 5A is a cross-sectional elevation of the feedthru 55 as taken along section line 5A-5A of FIG. 4. FIG. 5B is a longitudinal cross-sectional elevation of an alternative embodiment of the feedthru 55 as taken along section line 5B-5B of FIG. 2B, wherein the chip capacitors 90 are not shown for clarity purposes.

In one embodiment, as shown in FIGS. 2A, 3A and 4, the feedthru 55 includes a header side 95, a can side 100 and a lateral or edge side 105 that forms a rectangular or square edge or boarder of the feedthru 55. As can be understood from FIGS. 2B, 3B and 5B, in an alternative embodiment, the edge side 105 may form a circular or rounded edge or boarder of the feedthru 55. As indicated in FIGS. 4 and 5A, the edge side 105 may vary in diameter to define a slot or groove 110 that receives the wall 65 of the can 15 when the feedthru 55 is assembled into the can 15 of the pulse generator 5.

As can be understood from FIGS. 2A-5B, the feedthru 55 includes a feedthru housing 115, a core 120, chip capacitors 90, tabs 70 and ground and power circuits. The housing 115 forms the edge side 105 of the feedthru 55 and includes a central or core-receiving opening 125. The housing 115 may be machined, molded or otherwise formed to fit the space and design constraints of an implantable pulse generator 5. The housing 115 may be titanium, a titanium alloy, MP35N, or stainless steel.

The outer edge or boundary of the housing 115 is defined by the edge side 105 and includes the groove or slot 110 that receives the can wall 65 when the feedthru is mounted in the can wall. The central opening 125 of the housing 115 extends axially through the housing and defines a void that is occupied by the core 120.

As shown in FIGS. 2A-5B, the core 120 includes a header face 130, a can face 135, and through-holes 140 extending axially therethrough. The core 120 may be formed of an electrically insulating material, such as ceramic, glass, or sapphire.

As can be understood from FIGS. 1-5B, the feedthru 55 includes a power circuit and a ground circuit. The power circuit includes the tabs 70, their respective vias 142 and power traces 150. The tabs 70 are electrically coupled to each other by their respective vias 142, and the power traces 150 electrically couple the tabs 70 to the power sides 92 of the chip capacitors 90 located on the feedthru 55. The power circuit, via the tabs 70, electrically couples the power sides of the electrical components 17 housed in the can wall 65 to the lead connector blocks 20 of the header 10.

The ground circuit includes the feedthru housing 115 and ground traces 145 electrically coupled to the feedthru housing 115. The ground traces 145 electrically couple the ground sides 91 of the chip capacitors 90 to the feedthru housing 115, which is electrically coupled to the can wall 65. A detailed discussion regarding each of the components of the power and ground circuits is given below.

As indicated in FIGS. 2A-5B, the electrically conductive tabs 70 may be located on one or both of the faces 130, 135 of the core 120. For example, tabs 70 may be located near each of the four corners of each face 130, 135. The tabs 70 may be arranged such that a tab 70 on the header face 130 near a first corner of the feedthru 55 is located directly across the core from a tab 70 mounted on the can face 135 near the same first corner, thereby forming a pair of tabs 70. Such a paired arrangement may be provided at each of the four corners of the feedthru 55.

While in some embodiments, as illustrated in FIGS. 2A-3B, the tabs 70 are located near outside edges of the core header face 130 and core can face 135, in alternative embodiments, the tabs 70 may be located closer to the centers of the core header face 130 and core can face 135. In still other embodiments, tabs 70 may be located near both the centers and the outside edges of the core header face 130 and core can face 135. In other embodiments, the tabs 70 may be located in other configurations or locations as long as there is sufficient space for connection of the conductors 60, 62 to the tabs 70.

As can be understood from FIGS. 2A-3B, the number of tabs 70 on the core header face 130 generally corresponds to the number of tabs 70 on the core can face 135. In one embodiment, there are four tabs 70 on the core header face 130 and a corresponding four tabs 70 on the core can face 135. In some embodiments, there are less than four tabs 70 or more than four tabs 70 on each of the core header face 130 and the core can face 135.

Figure 6A:
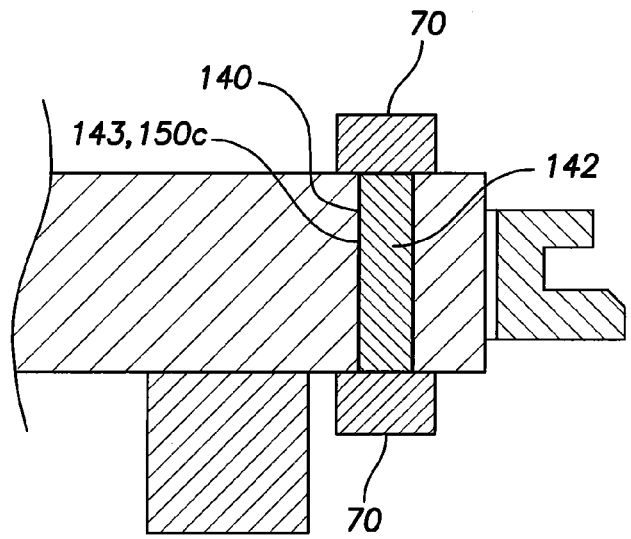
FIGS. 6A-6F are cross-sectional views of alternative tab/via configurations as if viewed in region A of FIG. 5A.

As indicated in FIGS. 5A and 5B, electrically conductive vias 142 extend through the through-holes 140 to electrically couple together the tabs 70 of each pair of tabs 70. The vias 142 and the associated tabs 70 may have a variety of configurations as shown in FIGS. 6A-6F, which are cross-sectional views of alternative tab configurations as if viewed in region A of FIG. 5A. For example, as indicated in FIG. 6A, the vias 142 may be a solid member 142 formed of electrically conductive material such as titanium, stainless steel, MP35N, etc. or a solid member formed of electrically or non-electrically conductive material coated with an electrically conductive material, such as gold, nickel, platinum, etc., where such coating is provided via electroplating, photo deposition, vapor deposition, etc. The surfaces of the through-holes 140 may additionally be coated with an electrically conductive material 143, such as gold, nickel, platinum, etc., where such coating is provided via electroplating, photo deposition, vapor deposition, etc. Such solid member vias 142 may be brazed (including gold brazed), welded or epoxied into the through-holes 140.

Figure 6B:
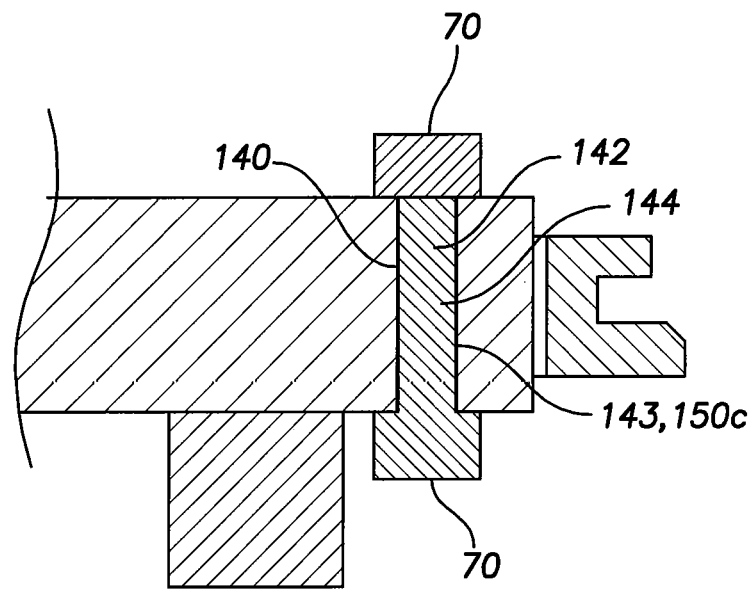
Figure 6C:
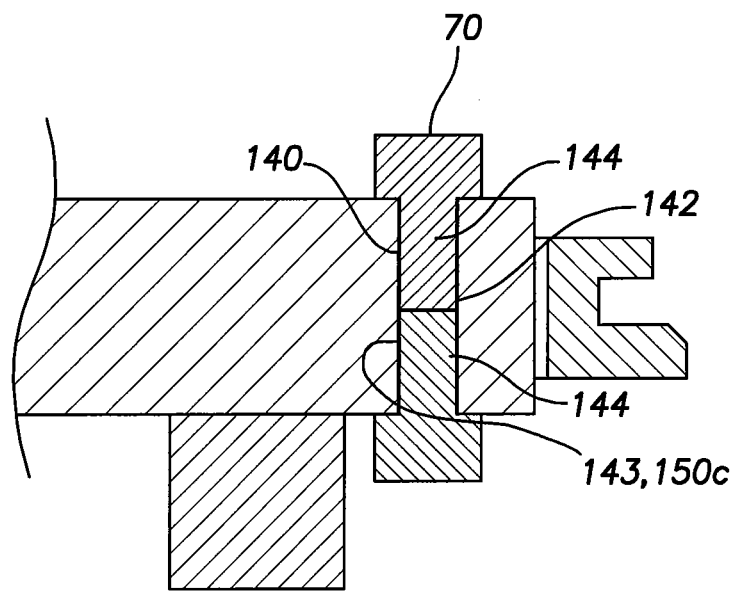

While the solid member vias 142 depicted in FIG. 6A may be a body that is a separate piece from the tabs 70 such that generally no portion of a tab 70 extends into a through-hole 140. As shown in FIGS. 6B and 6C, a portion 144 of a tab 70 may extend into the through-hole 140 to form at least a portion of a solid member via 142. For example, as depicted in FIG. 6B, the entirety of a solid member via 142 may be an extension 144 of a tab 70. Similarly, as illustrated in FIG. 6C, a portion of a solid member via 142 may be an extension 144 of both its respective tabs 70, each tab forming a portion of the solid member via 142. The tab 70 may also be a continuous, solid body extending all the way through the core 120 and also forming the solid member via 142. As shown in FIG. 6F, the diameter of the tab 70 may be the same as the diameter of the via 142. As can be understood from FIG. 6F, such a continuous, solid body tab 70 may be brazed to the through-hole 140 of the core 120. The solid body tab 70 may be made of titanium, MP35N, stainless steel, etc.

Figure 6D:
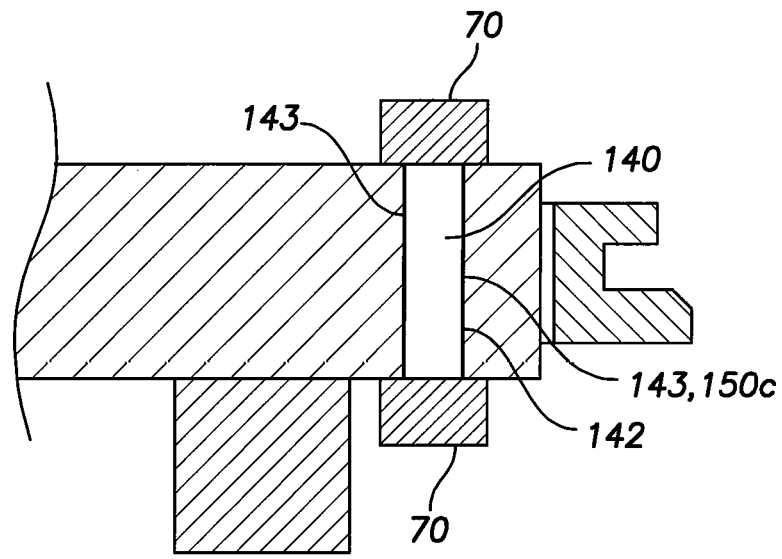

As shown in FIG. 6D, the vias 142 may be a hollow shaft extending axially through the core 120, wherein the surfaces of the hollow shafts are coated with an electrically conductive material 143 to form an electrically conductive trace or coating over on the surfaces of the hollow shafts. The vias 142 may be brazed, welded or secured to the tabs 70 via an electrically conductive epoxy.

Figure 6E:
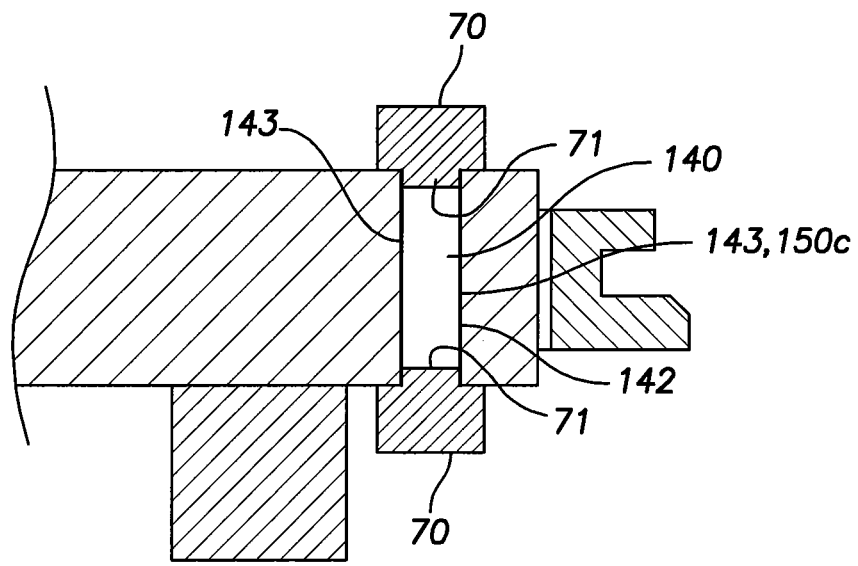
Figure 6F:
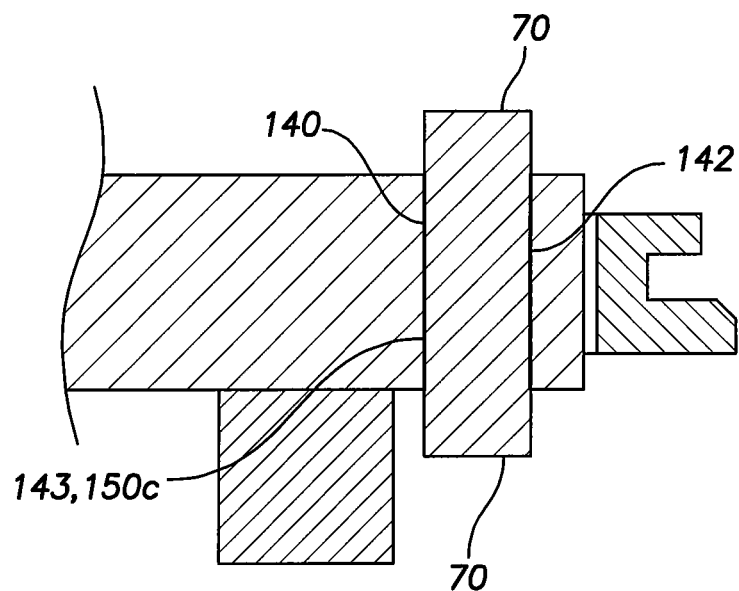

As shown in FIG. 6E, in the vias 142 and tabs 70 may be a combination of the concepts shown in FIGS. 6B-6D, such that the tabs 70 partially extend into the through-holes 140 as nubs 71 and the through holes 140 with their electrically conductive coatings that serve as vias 142 complete the electrical connections between opposed nubs 71. Thus, the vias 142 could be described as a combination of electrically conductive coatings and nubs.

As can be understood from FIGS. 1 and 2A and 2B, conductors 60 leading to the connector blocks 20 are electrically connected via welding, brazing, etc. to the tabs 70 on the header face 130 of the core 120. In a similar fashion and as can be understood from FIGS. 1 and 3A and 3B, conductors 62 leading to the electrical components 17 (e.g. the output flex, hybrid, etc.) housed in the can 15 are electrically connected via welding, brazing, etc. to the tabs 70 on the can face 135 of the core 120. Thus, the tabs 70 and vias 142 provide an electrical pathway through the feedthru 55 to electrically couple the conductors 60, 62 and the connector blocks 20 and components 17 electrically coupled to the conductors 60, 62. As can be understood from FIGS. 1-5B, in at least some of the embodiments of the feedthrus 55 disclosed herein, the feedthrus 55 do not employ feedthru wires.

As can be understood from FIG. 5A, the tabs or posts 70 have a height $H_T$ of between approximately 0.01 in. and approximately 0.05 in. and a diameter $D_T$ of between approximately 0.03 in. and approximately 0.05 in. In one embodiment, the tabs or posts 70 have a height $H_T$ of approximately 0.02 in. and a diameter $D_T$ of approximately 0.03 in. The tabs 70 may be formed of titanium, kovar, stainless steel, MP35N, platinum or gold. The tabs 70 may be brazed, welded or secured to the core faces 130, 135 via an electrically conductive epoxy. In one embodiment, the via 142 may have a length that is generally the same as the thickness of the core 120, e.g., 0.06 in. In one embodiment, the via 142 may have a diameter of 0.015 in.

Figure 7A:
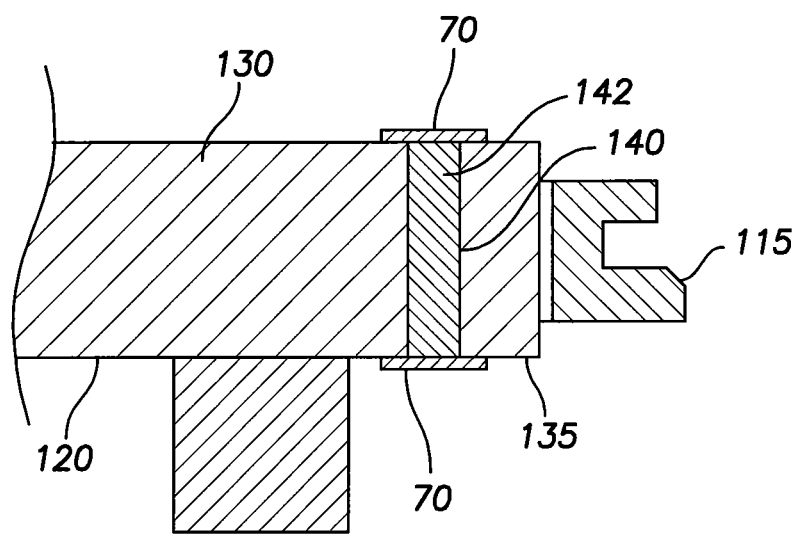
FIG. 7A is a cross-sectional view of a low-relief generally flush tab configuration as if viewed in region A of FIG. 5A.
Figure 7B:
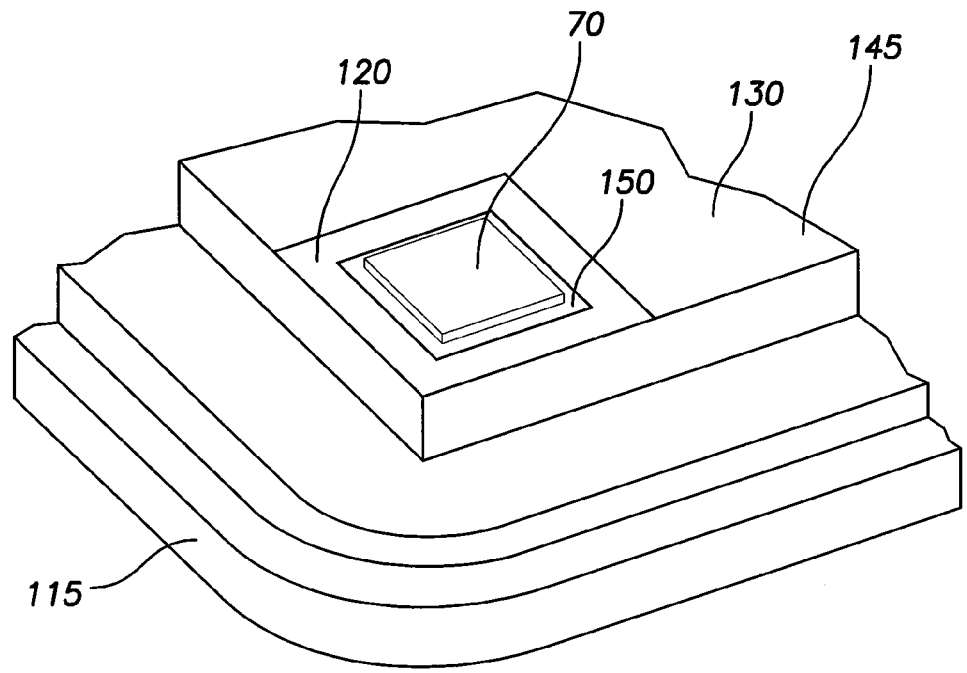
FIG. 7B is an isometric view of the tab configuration of FIG. 7A as if viewed in region B of FIG. 2A.
Figure 7C:
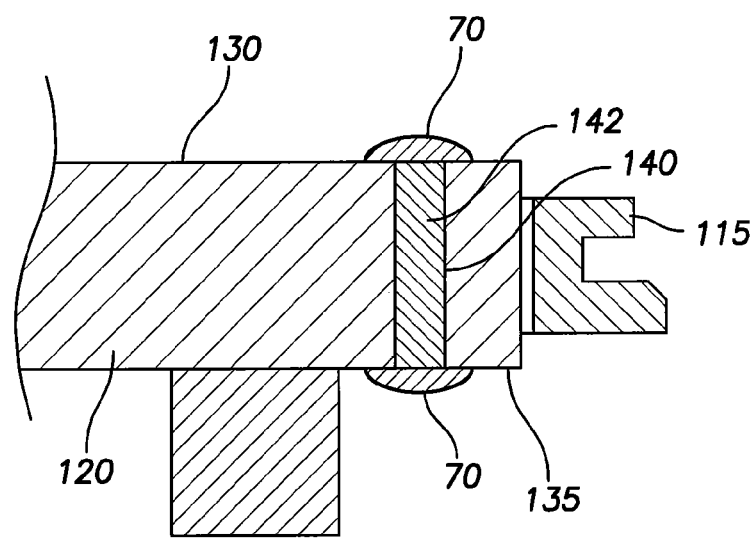
FIG. 7C is a cross-sectional view of a low-relief bump tab configuration as if viewed in region A of FIG. 5A.
Figure 7D:
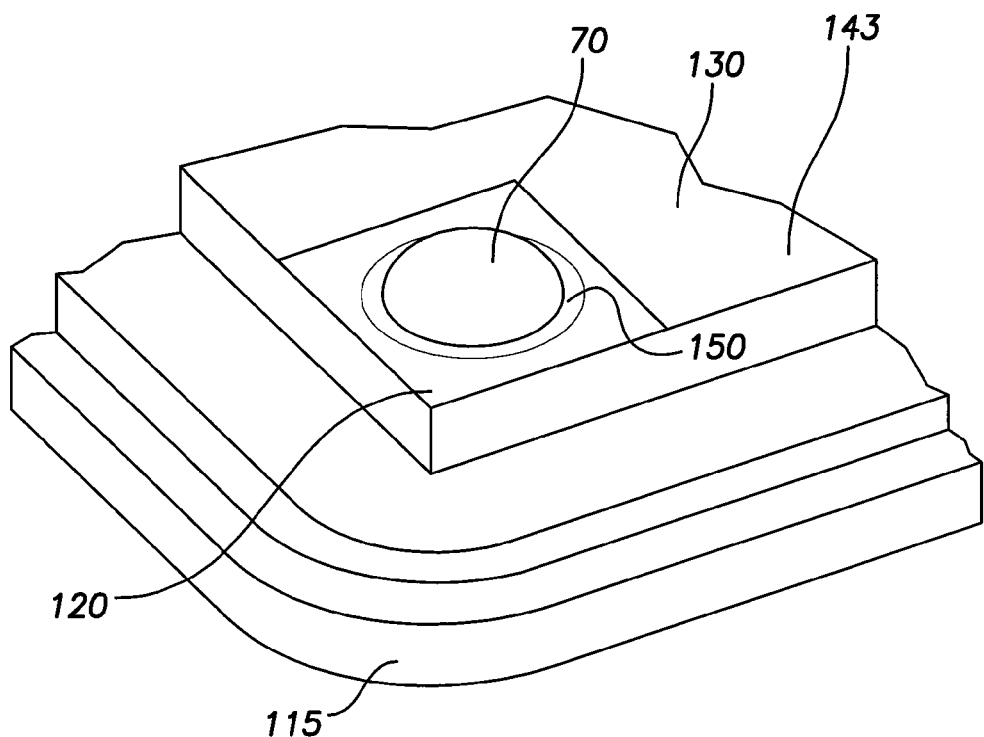
FIG. 7D is an isometric view of the tab configuration of FIG. 7C as if viewed in region B of FIG. 2A.

In some embodiments, as can be understood from FIGS. 7A-7D, which are cross sectional and isometric views, the tabs 70 may have a low surface relief. In some low-relief embodiments, as shown in FIGS. 7A-7B, the tabs 70 may appear flat and perhaps even nearly flush with the core header and can surfaces 130, 135 on which the tabs 70 are mounted. In some other low relief embodiments, as depicted in FIGS. 7A-7B, the tabs 70 may be slightly raised to be bump-like. In any of the embodiments depicted in FIGS. 7A-7D, the low relief tabs 70 may have a circular, rectangular or some other configuration. The low relief tabs 70, whether flush or bump-like, simply serve as locations or features for welding, brazing or other types of attachment to the conductors 60, 62 of the header 10 and can 15.

In some embodiments, as can be understood from FIGS. 2A and 5A and 5B, the tabs 70 may have a post-like configuration that projects a small distance from the core header and can surfaces 130, 135 on which the tabs 70 are mounted and, as a result, are less low-relief than the embodiments discussed with respect to FIGS. 7A-7D. As indicated in FIGS. 2A and 5A, the post-like tabs 70 may be box-like or cubical in shape.

Figure 7E:
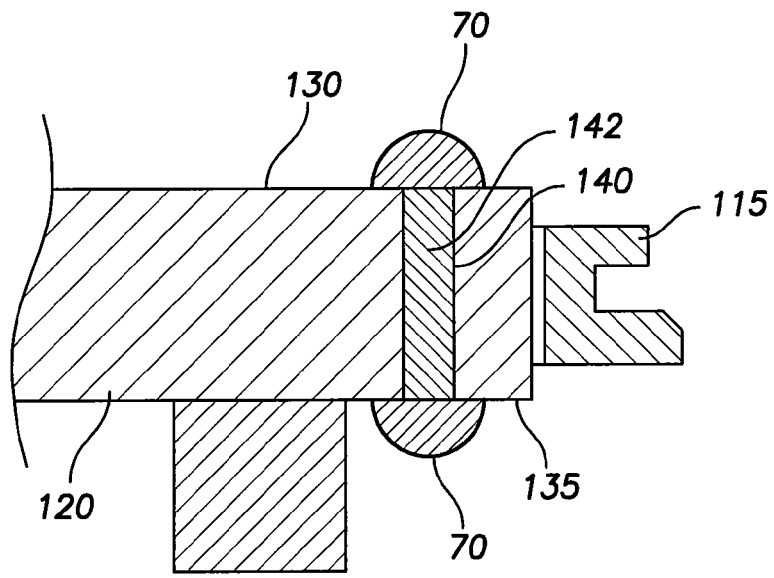
FIG. 7E is a cross-sectional view of post-type tab having a spherical configuration as if viewed in region A of FIG. 5A.
Figure 7F:
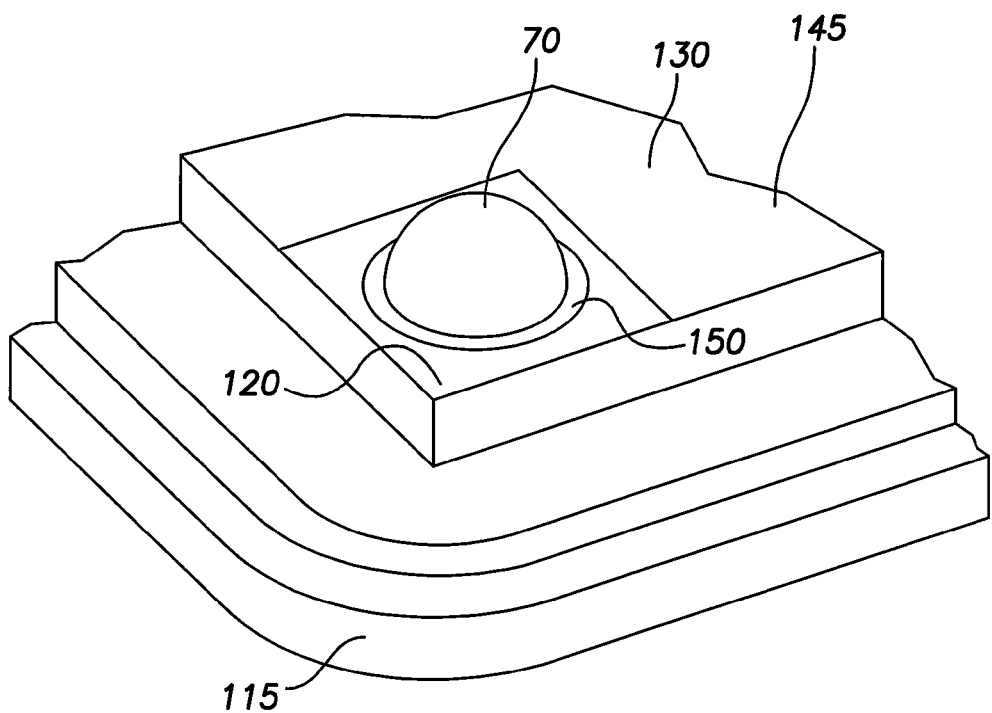
FIG. 7F is an isometric view of the tab configuration of FIG. 7E as if viewed in region B of FIG. 2A.
Figure 7G:
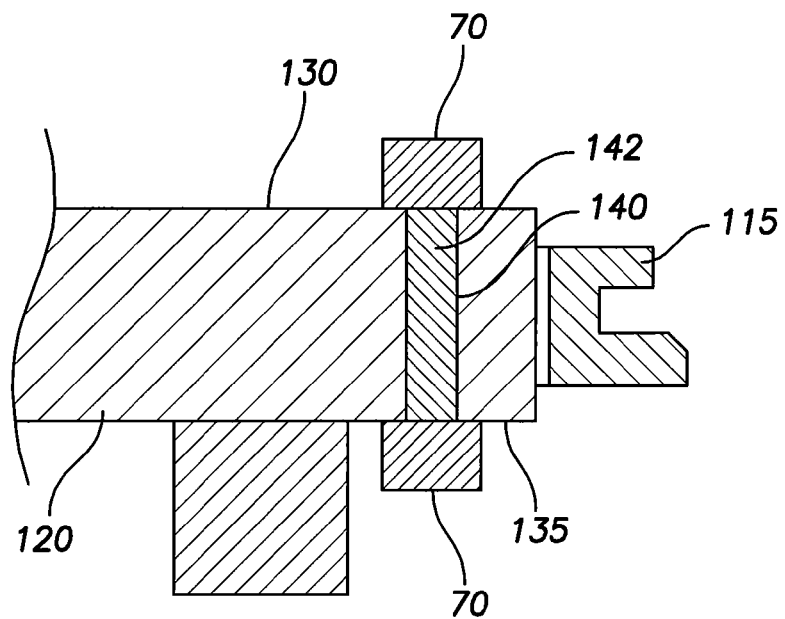
FIG. 7G is a cross-sectional view of a post-type tab having a cylindrical configuration as if viewed in region A of FIG. 5A.
Figure 7H:
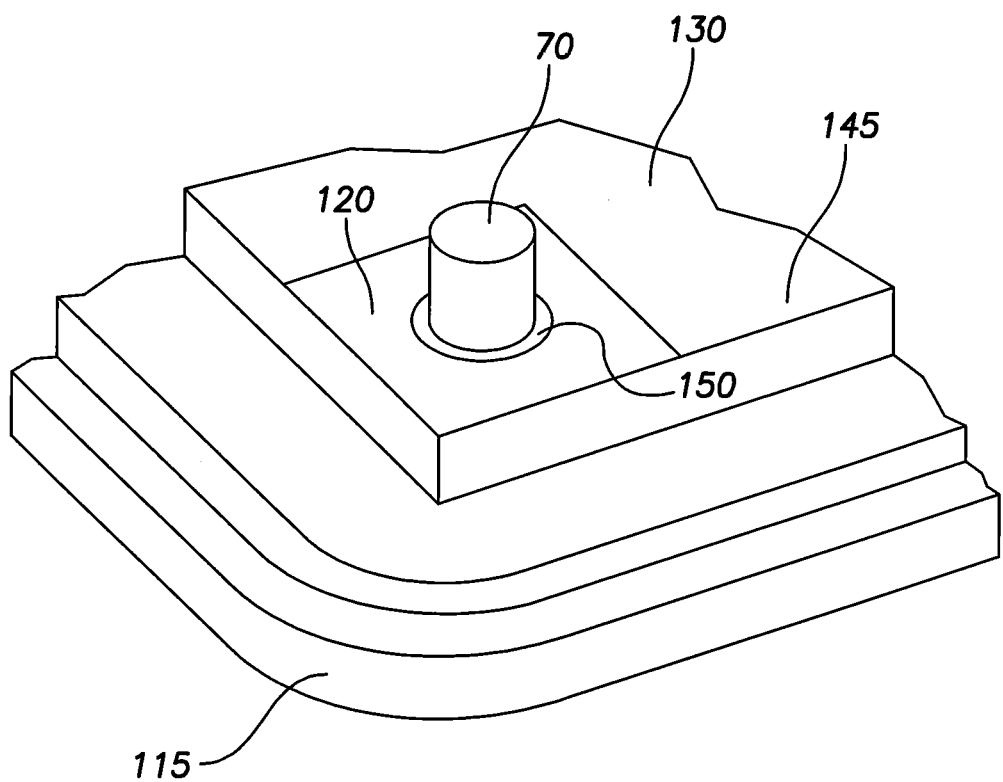
FIG. 7H is an isometric view of the tab configuration of FIG. 7G as if viewed in region B of FIG. 2A.

As can be understood from FIGS. 7E-7H, which are cross sectional and isometric views, the post-like tabs 70 may have other shapes or configurations. For example, as shown in FIGS. 7E-7F, the post-like tabs 70 may be half spherical or another rounded shape. As shown in FIGS. 7G-7H, the post-like tabs 70 may have a cylindrical shape. In other embodiments, the post-like tabs 70 may have other shapes or configurations, such as cubical, half-spherical, cylindrical or some other shape. The post-type tabs 70, whether cubical, half-spherical, cylindrical or some other shape, simply serve as locations or features for welding, brazing or other types of attachment to the conductors 60, 62 of the header 10 and can 15.

While the tab configurations illustrated in FIGS. 2A and 2B, 5A and 5B and 7A-7H show matching tab configurations on each side of the core, in various embodiments, any one, two or more tab configurations depicted in FIGS. 2A and 2B, 5A and 5B and 7A-7H may be combined on a single feedthru 55 or paired with a single via 142. Similarly, while the via configuration depicted in FIGS. 5A and 5B show matching via configurations, any of one, two or more via 142 configurations depicted in FIGS. 6A-6F may be used on a single feedthru 55.

As can be understood from FIGS. 2A and 3A, the outer boarder or edge surface of the core 120 is rectangular and, in one embodiment, square. In an alternative embodiment, as shown in FIGS. 2B and 3B, the outer edge is round or circular. As shown in FIGS. 2A-3B, the outer edge surface of the core 120 projects a small amount past the housing 115 on both the header and can sides 95, 100 of the feedthru such that the outer edge surface of the core 120 is partially exposed and not entirely within housing 115.

As indicated in FIGS. 2A-3B, an electrically conductive ground coating or trace 145 extends over the core outer edge surface, a substantial portion of the core header face 130, and a smaller portion of the core can face 135. In one embodiment, the core header face 130 is generally entirely coated with the ground trace 145a, except in small regions 143 surrounding the tabs 70, wherein the small regions 143 are exposed surfaces of the core 120 electrically isolating the tabs 70 from the ground trace 145.

The ground trace 145b extends along the core outer edge from the core header face 130 to generally cover the entire surface of the core outer edge. The ground trace 145b extending over the core outer edge is in electrical contact with, and brazed or welded to, the housing 115, which is in electrical contact with the can wall 65. The can wall 65 serves as the ground for the pulse generator 5.

The ground trace 145c extends across the center of the core can face 135 from the core outer edge in the form of a rectangular trace 145c, in the context of FIG. 3A, and a round trace 145c, in the context of FIG. 3B. Chip capacitors 90 are located on the core can face 135. The ground trace 145 in all of its locations acts as a portion of the ground circuit, coupling the ground sides 91 of the chip capacitors 90 to the can wall 65 via the feedthru housing 115, which is another portion of the ground circuit. The can wall 65, which is electrically coupled to the feedthru housing 115, serves as the ground for the pulse generator 5. The ground trace 145 in any of its locations may be made of gold, platinum, nickel, titanium, or MP35N. The ground trace 145 in any of its locations may be formed via any method, including photo etching, deposition, electroplating, etc.

As shown in FIGS. 2A and 2B, an electrically conductive power coating or trace 150a boarders each tab 70 and is separated from the adjacent ground trace 145a, 145b by an exposed region 143 of the surface of the electrically insulating core 120. As indicated in FIGS. 3A and 3B, an electrically conductive power trace 150b extends across the core can face 135 from a tab 70 surrounded by the power trace 150b to a power side 92 of a chip capacitor 90. The power trace 150b may extend along the core can face 135 in the form of a rectangle or an oval or other suitable shape.

As indicated in FIGS. 5A-6D, power traces 150c, in the form of electrically conductive coatings 143, may extend along the vias 142 and/or the surfaces of the through-holes 140 to join with the power traces 150a, 150b on the core header and can sides 130, 135. The power traces 150a, 150b, 150c form a power side electrical circuit, along with the tabs 70 and vias 142, that electrically couples the power sides 92 of the chip capacitors 90 with the connector blocks 20 and electrical components 17 via the conductors 60, 62. The power traces 150 may be formed of any electrically conductive material (e.g. gold, platinum, nickel, titanium, MP35N, etc.) capable of being formed into a trace via any method including photo etching, deposition, electroplating, etc.

As can be understood from FIGS. 2A-3B and with reference to FIG. 1, the tabs 70 on the core header face 130 may be electrically connected to the connector blocks 20 by conductors 60, such as round wires, flat ribbon wires or flex cables. At the core can face 135, the tabs 70 may be electrically connected to the electrical components 17 by conductors 62, such as round wires, flat ribbon wires or flex cables or to electrically conductive traces on a printed circuit board. Because the tabs 70 may be electrically connected to each other by vias 142 and electrically connected to the header and can components 20, 17 by less expensive conductors, expensive feedthru wires, such as Pt/Ir wires, are not required in embodiments of the feedthru 55. Therefore, such feedthrus 55 have reduced material and manufacturing costs.

As illustrated in FIGS. 3A and 3B, the chip capacitors 90 on the core can face 135 of may include a ground end 91 and a power end 92. The ground end 91 of the chip capacitor 90 is electrically connected to the ground trace 145. The power end 92 of the chip capacitor 90 is electrically connected to the power trace 150. In one embodiment, a first chip capacitor 90 is separated from a second chip capacitor 90 by a minimum of approximately 0.03 in.

The chip capacitors 90 are easy to obtain, that is, they are readily commercially available or "off-the-shelf" chip capacitors. For example, the chip capacitors 90 may be obtained as model 0805 chip capacitor as manufactured by NovaCap of Valencia, Calif. 91355. The chip capacitors 90 are a part of the EMI filter element. EMI is a (usually undesirable) disturbance caused in a radio receiver or other electrical circuit by electromagnetic radiation emitted from an external source. Such a signal may interfere with the electrical components in the can of the implantable pulse generator. Thus, an EMI filter element, such as a chip capacitor, may reduce or eliminate the interference caused by an EMI. Additionally, an "off-the-shelf" chip capacitor may be less expensive and easier to obtain than a discoidal filter assembly, thus reducing the design and manufacturing costs of the feedthru 55.

As can be understood from FIGS. 4 and 5A and 5B, to assemble the feedthru 55, the housing 115 and core 120 may be connected by soldering, brazing, welding or other suitable method to form a housing-core assembly. The coupling of the core 120 to the housing 115 creates a hermetic seal. The tabs 70 may be connected to the core 120 by brazing, soldering, welding or other suitable method. The chip capacitors 90 may be surface mounted or otherwise connected to the can end 135 of the core 120 by soldering, electrically conductive epoxy or other suitable method.

As can be understood from FIGS. 2A-3B, and with reference to FIG. 1, the feedthru 55 is assembled into the can wall 65 and electrically coupled to the electronic components 17 in the can 15 and the lead connector blocks 20 in the header 10. The can wall 65, which is electrically coupled to the feedthru housing 115, is in electrical communication with the ground side 91 of the chip capacitor 90 via the ground circuit extending through the feedthru housing and ground trace 145. Similarly, to the electronic components 17 in the can 15 and the lead connector blocks 20 in the header 10 are in electrical communication with each other and the power side 92 of the chip capacitor 90 via the power circuit formed by the tabs 70, their respective vias 142 and the power trace 150.

Figure 8A:
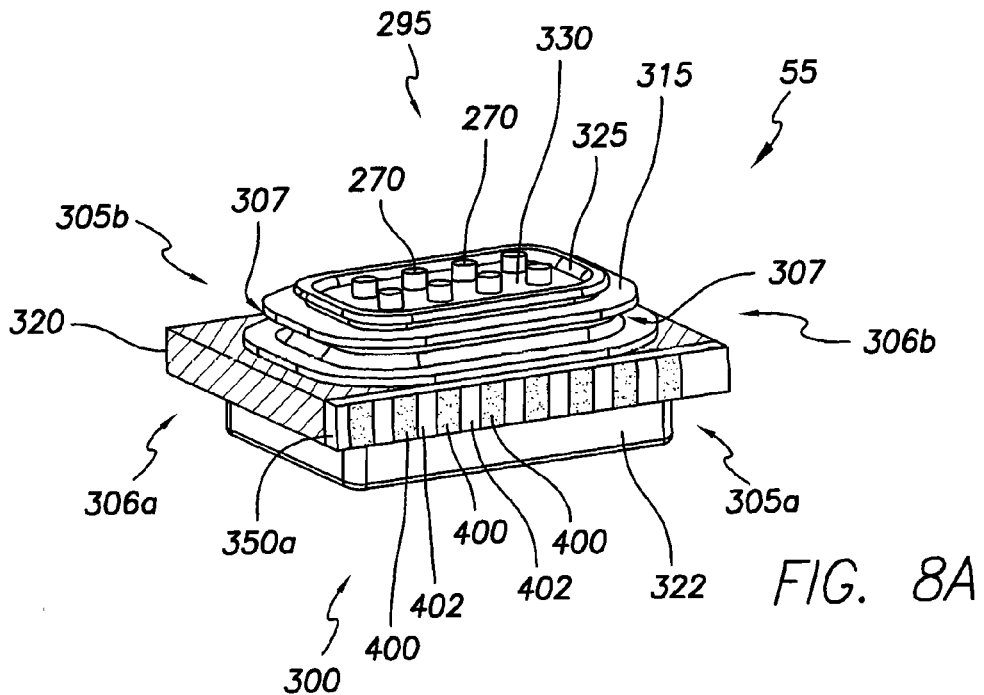
FIG. 8A is a side-top isometric view of the feedthru.
Figure 8B:
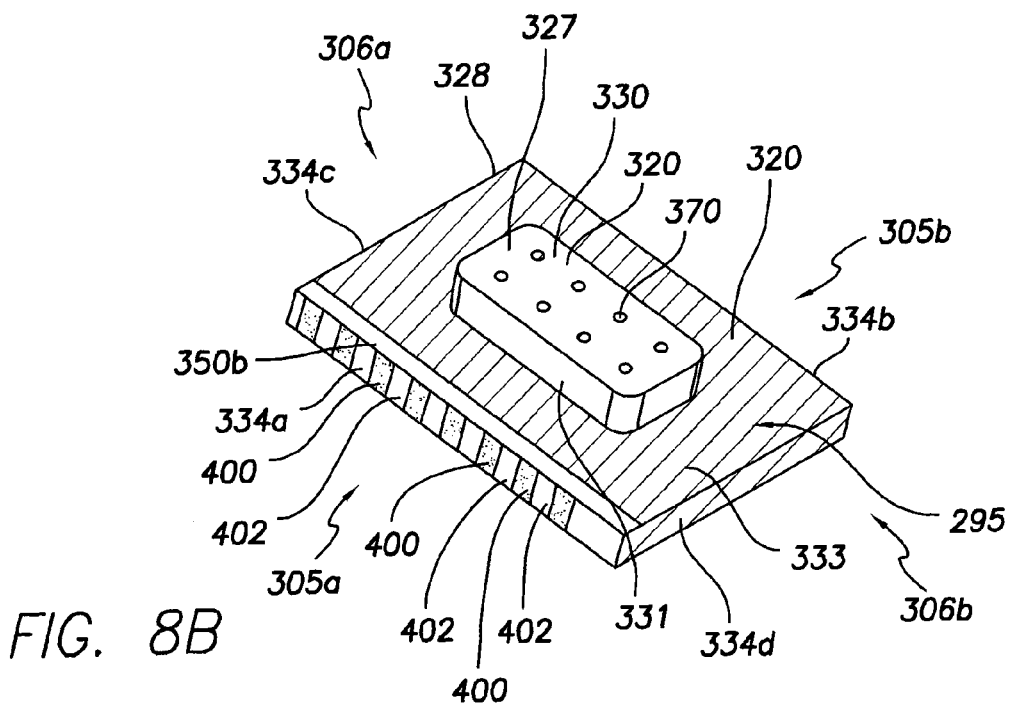
FIG. 8B is another side-top isometric view of the feedthru with the housing hidden to reveal the core.
Figure 8C:
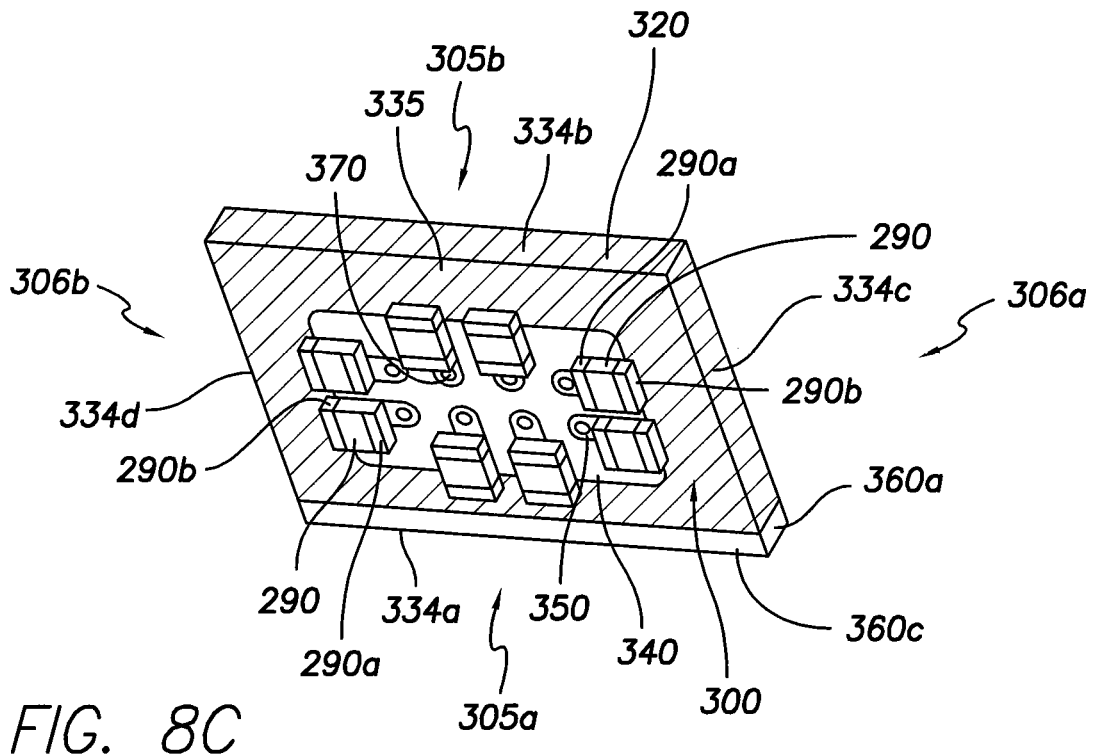
FIG. 8C is a side-top isometric view of the feedthru with the shield hidden to reveal the chip capacitors.
Figure 8D:
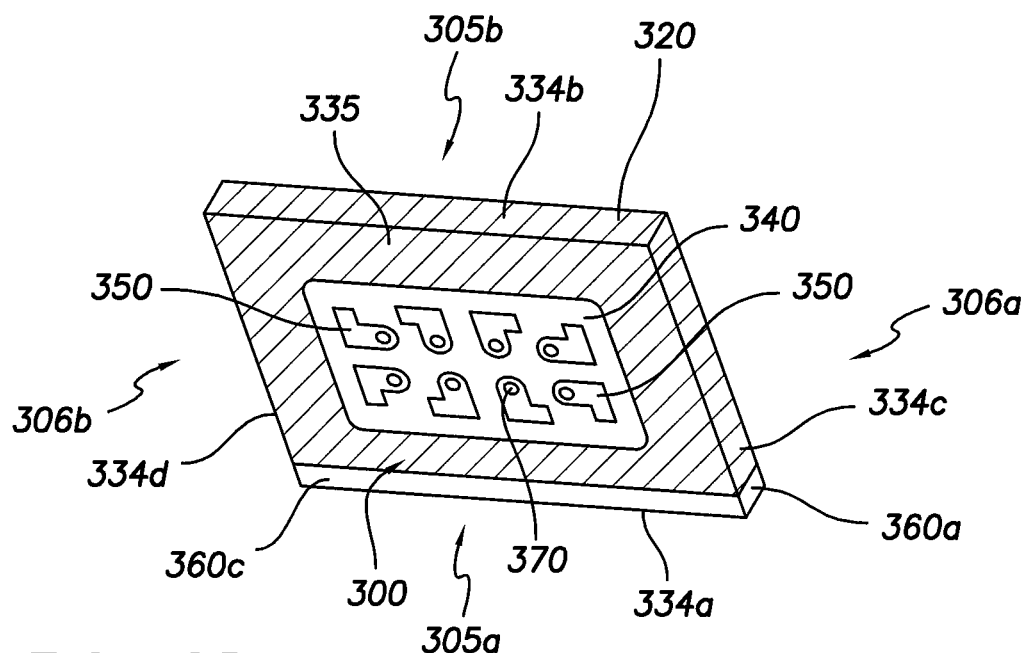
FIG. 8D is the same view as FIG. 8C, except the chip capacitors are hidden to reveal the power traces.
Figure 9A:
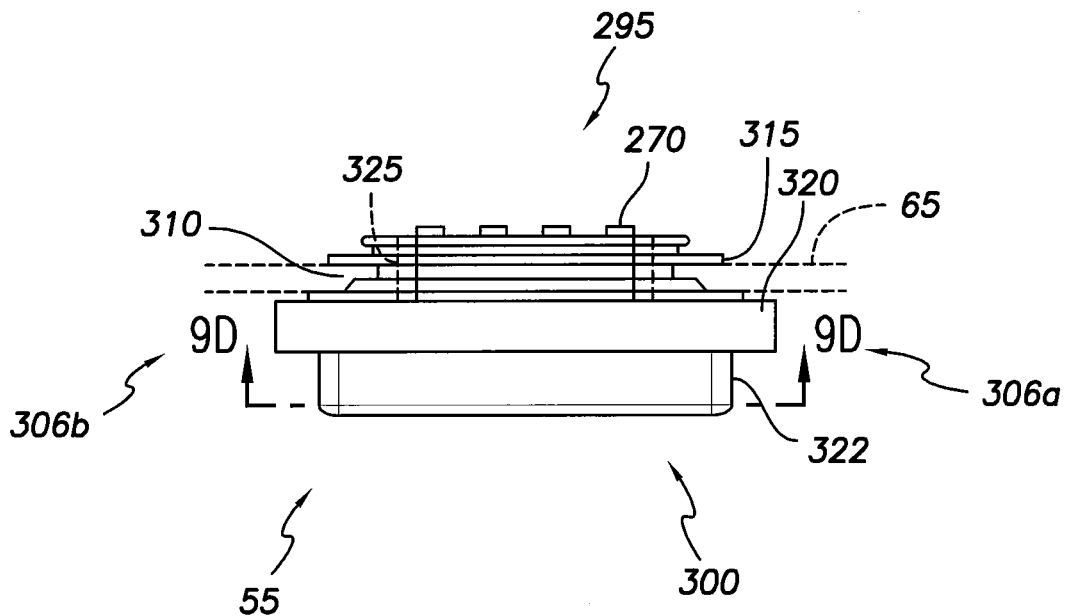
FIG. 9A is an elevation view of the non-contact side of the feedthru.
Figure 9B:
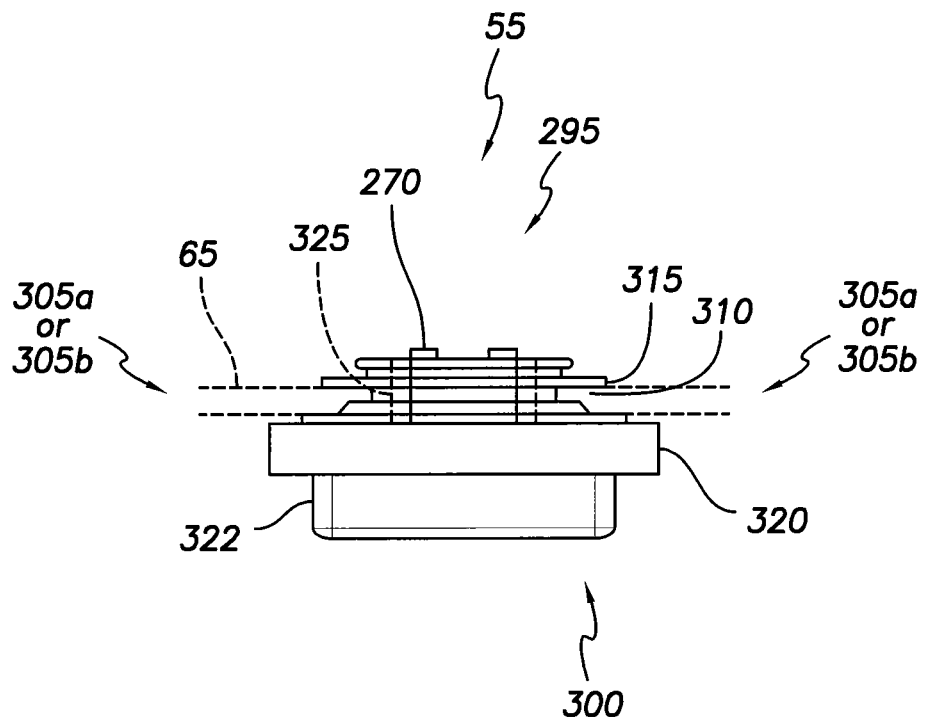
FIG. 9B is an elevation view of one of the ends of the feedthru.
Figure 9C:
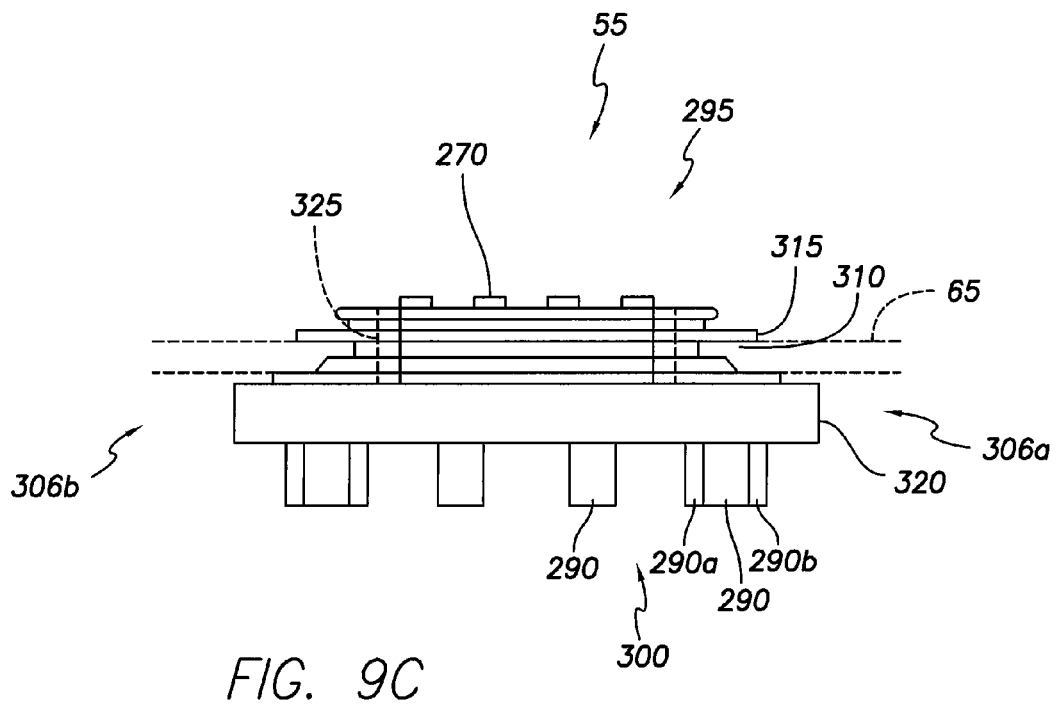
FIG. 9C is the same elevation view of FIG. 9A, less the shield.
Figure 9D:
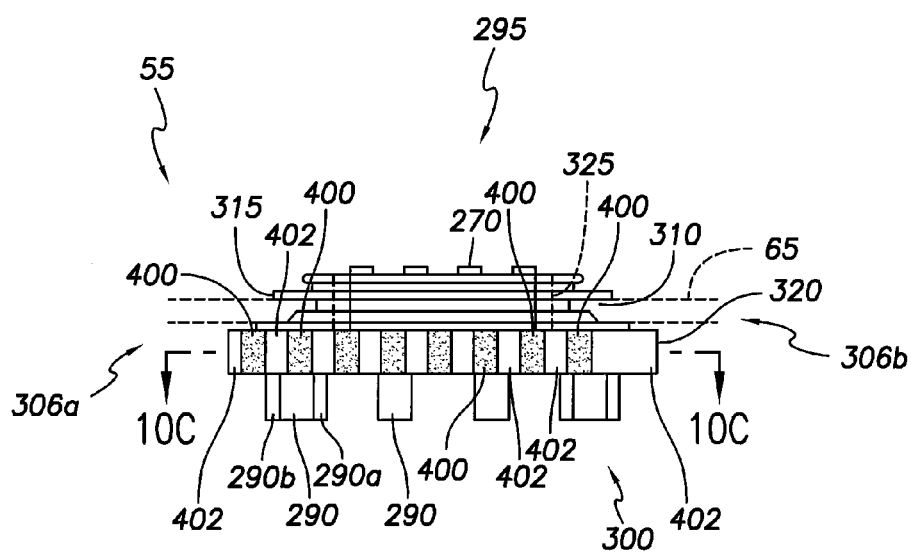
FIG. 9D is an elevation view of the contact side of the feedthru, less the shield.

To begin a detailed discussion regarding another embodiment of a feedthru 55 that may be employed with a pulse generator 5 similar to that depicted in FIG. 1, reference is now made to FIGS. 8A-8D and 9A-9D. FIG. 8A is a side-top isometric view of the feedthru 55, and FIG. 8B is another side-top isometric view of the feedthru 55 with the housing 315 hidden to reveal the core 320. FIG. 8C is a side-top isometric view of the feedthru 55 with the shield 322 hidden to reveal the chip capacitors 290, and FIG. 8D is the same view as FIG. 8C, except the chip capacitors 290 are hidden to reveal the power traces 350. FIGS. 9A and 9B are, respectively, an elevation view of the non-contact side 305b of the feedthru 55 and an elevation view of one of the ends (306a or 306b) of the feedthru 55. FIGS. 9C and 9D are, respectively, the elevation view of FIG. 9A less the shield 322 and an elevation view of the contact side 305a of the feedthru 55 less the shield 322.

In one embodiment, as shown in FIGS. 8A-9D, the feedthru 55 includes a header side 295, a can side 300, a contact side 305a, a non-contact side 305b, and first and second ends 306a, 306b. As can be understood from FIGS. 8A-8C, the overall configuration of the feedthru 55 may be generally rectangular in some embodiments. However, in other embodiments, similar to as discussed above with respect to the preceding embodiments, the feedthru 55 may have other configurations.

As illustrated in FIGS. 8A-9D, in one embodiment, the feedthru 55 includes a feedthru housing 315, a core 320, a shield 322, chip capacitors 290, tabs 270 and ground and power circuits. The housing 315 has an outer contoured side 307 and a central or core-receiving opening 325. The contoured side 307 of the housing 315 includes the groove or slot 310 that receives the can wall 65 when the feedthru is mounted in the can wall. The central opening 325 of the housing 315 extends axially through the housing and defines a void that is occupied by the core 320, or more specifically, as described below, an upper portion 327 of the core 320. The housing 315 may be machined, molded or otherwise formed to fit the space and design constraints of an implantable pulse generator 5. The housing 315 may be titanium, a titanium alloy, MP35N, or stainless steel.

As can be understood from FIG. 8B, in one embodiment, the core 320 includes an upper necked-down portion 327 extending from a bottom base portion 328. As indicated in FIGS. 8B-8D, the upper portion 327 includes a header face 330 and sides 331, and the base portion 328 includes an upper surface 333, side surfaces 334a, 334b, end surfaces 334c, 334d, and a can face 335. The sides 331 of the upper portion 327 extend generally perpendicularly between the header face 330 and the upper surface 333 of the base portion 328. The sides 331 of the upper portion 327 are configured such that the upper portion 327 may be matingly received in the core-receiving opening 325 of the housing 315. When the upper core portion 327 is fully received in the core-receiving opening 325, a bottom surface or boundary of the housing 315 may abut against the upper surface 333 of the core base portion 328, as indicated in FIGS. 8A and 9A-9D. The core 320 may also include vias or through-holes 370 extending axially therethrough. The core 320 may be formed of an electrically insulating material, such as ceramic, glass, sapphire, ceramic 99% minimum pure alumina, or etc.

As can be understood from FIGS. 8A-8D, an electrically conductive material (represented by the cross-hatching in FIGS. 8A-8D) may extend across and form at least a portion of one or more of the following surfaces of the base portion 328 of the core 320: the upper surface 333; the side surface 334b corresponding to the non-contact side 305b of the feedthru 55; the end surfaces 334c, 334d; and the can face 335. Where the surfaces 333, 334b, 334c and 335 or at least portions thereof are formed by the conductive material (represented by cross-hatching), the surfaces 333, 334b, 334c and 335 or at least portions thereof may be electrically conductive and form at least a portion of a ground circuit as discussed later in this Detailed Description. The electrically conductive material (represented by cross-hatching) may be formed of gold, nickel, platinum, electrolytic nickel and gold, etc., where such coating is provided via electroplating, photo deposition, vapor deposition, etc. In one embodiment, the conductive material shall be in the form of a plating having a minimum thickness of 75 micro inches.

As indicated in FIG. 8B, in one embodiment, the conductive material (represented by cross-hatching) may extend across the entirety of an end surface 334d. However, as indicated in FIGS. 8A, 8C and 8D, the conductive material (represented by cross-hatching) may extend across less than the entirety of an end surface 334c, ending a short distance from the side surface 334a corresponding to the contact side 305a of the feedthru 55 such that this region 360a of the side surface 334c may be the electrically insulating surface of the electrically insulating material forming the core 320, defining an electrical insulation surface 360a.

As indicated in FIG. 8B, in one embodiment, the conductive material (represented by cross-hatching) may extend across less than the entirety of the upper surface 333, ending a short distance from the side surface 334a corresponding to the contact side 305a of the feedthru 55 such that this region 360b of the upper surface 333 may be the electrically insulating surface of the electrically insulating material forming the core 320, defining an electrical insulation surface 360b. The upper portion 327 of the core 320 may be completely free of the conductive material (represented by cross-hatching).

As indicated in FIG. 8D, in one embodiment, the conductive material (represented by cross-hatching) may extend across the entirety of regions of the can face 335 near three of the four edges of the can face 335, a rectangular central region 340 of the can face 335 being free of the conductive material (represented by cross-hatching) such that the surface of the central region 340 may be the electrically insulating surface of the material forming the core 320. Near the fourth edge of the can face 335, the conductive material (represented by cross-hatching) extending across the can face 335 may end a short distance from the side surface 334a corresponding to the contact side 305a of the feedthru 55 such that this region 360c of the can face 335 may be the electrically insulating surface of the electrically insulating material forming the core 320, defining an electrical insulation surface 360c.

As shown in FIG. 8D, the central region 340 of the can face 335 may include one or more traces 350, which may be L-shaped or other shapes. Each trace 350 may be spaced apart from adjacent traces 350 and the electrically conductive material (represented by cross-hatching) surrounding the central region 340. The traces 350 may be formed of an electrically conductive material such as gold, nickel, platinum, etc., where such coating is provided via electroplating, photo deposition, vapor deposition, etc. Because the traces 350 are separated from each other and the electrically conductive material (represented by cross-hatching) surrounding the central region 340, each trace 350 is electrically isolated until a chip capacitor 290 is placed to extend between the trace 350 and the electrically conductive material (represented by cross-hatching) surrounding the central region 340, as illustrated in FIG. 8C. For example, a power side 290a of a chip 290 may be electrically connected to a respective trace 350, and a ground side 290b of the chip capacitor 290 may be electrically connected to a location on the electrically conductive material (represented by cross-hatching) surrounding the central region 340. Since the electrically conductive material (represented by cross-hatching) surrounding the central region 340 extends about the side surfaces 334b-334d to the upper surface 333, which is in electrical contact with the housing 315 that is in electrical contact with the can wall 65 (see FIGS. 9A-9D), the combination of the chip capacitor ground side 290b, the conductive surfaces 334b-334d and 333 of the core 320, the housing 315, and the can wall 65 may form the ground circuit of the feedthru 55 and the pulse generator 5.

As can be understood from FIGS. 8A, 9A and 9B, the shield 322 may extend downward from, and be in electrical contact with, the electrically conductive material (represented by cross-hatching in FIGS. 8C and 8D) of the can face 335. The shield 322 may further extend below the capacitor chips 290 to totally enclose the capacitor chips 290 in a volume defined by the interior of the shield 322 and the can face 335. The shield 322 may be formed of titanium, stainless steel, nickel, etc., have a thickness of between approximately 0.005° and approximately 0.01" and be used to shield undesired EMI signals from entering the can 15.

The through-holes or vias 370 may terminate on the upper or header side of the feedthru 55 at the header face 330 of the core 320, as depicted in FIG. 8B. Similarly, each through-hole or via 370 may terminate on the bottom or can side of the feedthru 55 at the can face 335 of the core 320, as depicted in FIG. 8D. More specifically, as shown in FIG. 8D, a through-hole or via 370 may terminate in a portion of each trace 350.

Figure 10A:
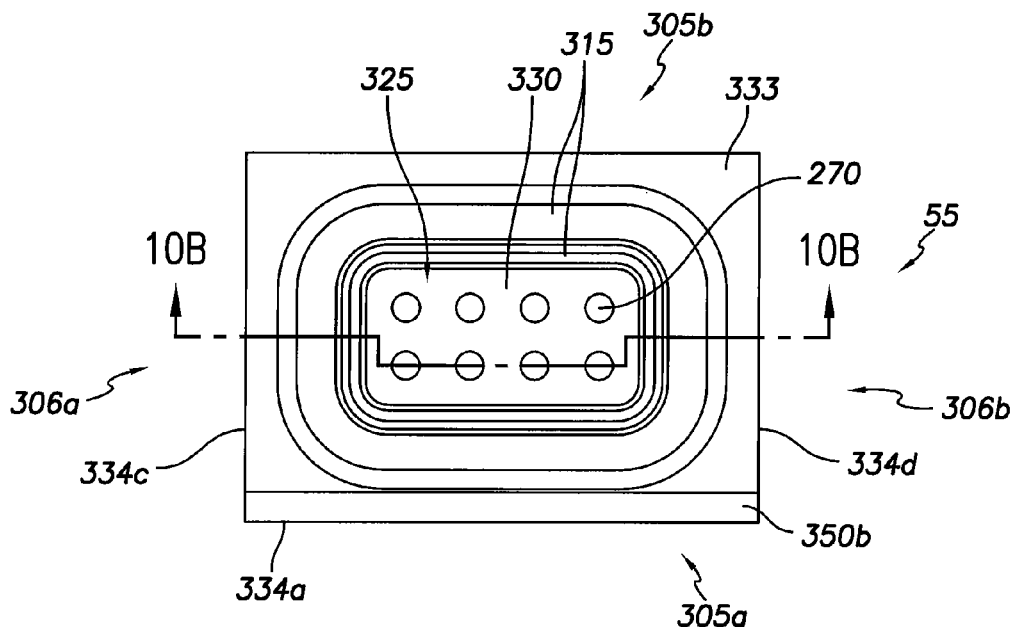
FIG. 10A is a plan view of the header side of the feedthru.
Figure 10B:
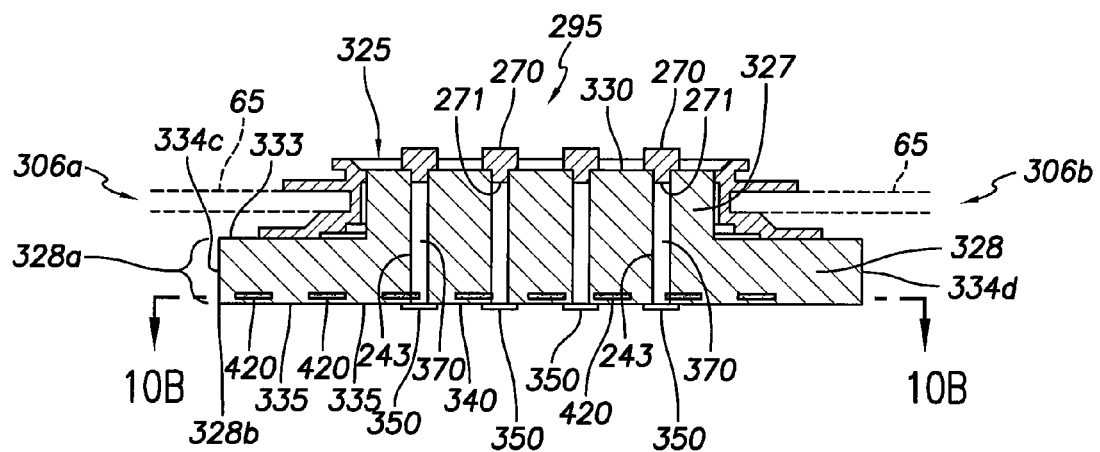
FIG. 10B is a longitudinal cross-section elevation of the feedthru as taken along section line 10B-10B in FIG. 10A.

As can be understood from FIG. 8A and FIG. 10A, which is a plan view of the header side of the feedthru 55, there may be one or more electrically conductive tabs 270 and, in one embodiment, there may be eight tabs 270 arranged in two spaced apart rows of four tabs 270. As indicated in FIGS. 8B and 8D, the electrically conductive vias 370 may be in a similar arrangement of two rows of four vias 370. Thus, a tab 270 may extend from the header side of each respective via 370. More specifically, as depicted in FIG. 10B, which is a longitudinal cross-section elevation of the feedthru 55 as taken along section line 10B-10B in FIG. 10A, a portion of each tab 270 may extend downward into the upper end of each respective via 370. In other embodiments, the tabs 270 and vias 370 may be located in other configurations or locations as long as there is sufficient space for connection of the conductors 60 (see FIG. 1) to the tabs 270 on the header side of the feedthru 55.

As indicated in FIG. 10B, in one embodiment, the electrically conductive tabs 270 and electrically conductive vias 370 may be configured in a manner similar to that discussed above with respect to FIG. 6E. Specifically, the tabs 270 may partially extend as nubs 271 into the vias 370. The vias 370 may be in the form of electrically conductive through-holes 370 lined with electrically conductive coatings 243 that serve as vias 370 that complete the electrical connections between the nubs 271 and the traces 350 in the central region 340 of the can side 300 of the feedthru 55. The surfaces of the through-holes 370 may be coated with an electrically conductive material 243, such as gold, nickel, platinum, etc., where such coating is provided via electroplating, photo deposition, vapor deposition, etc. The tabs 270 may be made of titanium, kovar, stainless steel, MP35N, platinum or gold. The nubs 271 may be brazed (including gold brazed), welded or epoxied into the through-holes 370.

In other embodiments, the vias 370 may be solid members distinct from, but electrically contacting, the tabs 270 and extending through the core 320 similar to those discussed above with respect to FIG. 6A. In such embodiments the solid member vias 370 may be formed of electrically conductive material such as titanium, stainless steel, MP35N, etc. or a solid member formed of electrically or non-electrically conductive material coated with an electrically conductive material, such as gold, nickel, platinum, etc., where such coating is provided via electroplating, photo deposition, vapor deposition, etc. Such solid member vias 370 may be brazed (including gold brazed), welded or epoxied into the holes in the core 320, and the tabs 270 may be similarly attached to the solid member vias.

In yet other embodiments, the vias 370 may be solid members that are extensions of the tabs 270 and extending through the core 320 similar to those discussed above with respect to FIGS. 6B and 6F. In yet other embodiments, the arrangement may be similar to that discussed above with respect to FIG. 6D, wherein the vias 370 may be through-holes 370 lined with an electrically conductive coating 243 (see FIG. 10B), but wherein the tabs 270 do not have nubs 271 or extensions that extend into the vias 370.

While the electrically conductive tabs 270 illustrated in FIG. 8A have a generally cylindrical shape similar to that described above with respect to FIGS. 7G and 7H, in other embodiments the tabs 270 may have other shapes. For example, the tabs 270 may have a hemispherical, reduced profile shape as discussed above with respect to FIGS. 7C and 7D, a less reduced profile hemispherical shape as discussed with respect to FIGS. 7E and 7F, a nub or planar configuration as discussed above with respect to FIGS. 7A and 7B, or a cubical or rectangular post like shape as discussed above with respect to FIGS. 2A and 5A. In other embodiments, the post-like tabs 270 may have other shapes or configurations, such as cubical, half-spherical, cylindrical or some other shape. The tabs 270 may have other configurations, and regardless of their shape, simply serve as locations or features for welding, brazing or other types of attachment to the conductors 60 of the header 10. While the via configuration and tab configuration depicted in FIGS. 8A and 10B are consistent among the pairs of vias and tabs, in other embodiments, the via and tab configurations employed for a single feedthru 55 may be of a variety of types and may be mixed and matched.

As shown in FIGS. 8A, 8B and 9D, the side surface 334a of the base portion 328 corresponding to the contact side 305a may include one or more electrical contact surfaces 400. For example, there may be a plurality of electrical contact surfaces 400 generally evenly distributed in a spaced-apart fashion along the length of the side surface 334a, the electrical contact surfaces 400 being electrically isolated from each other via insulation surfaces 402 located between each pair of electrical contact surfaces 400. As a result, the side surface 334a may have a striped arrangement of electrical contact surfaces 400 and electrical insulation surfaces 402. In one embodiment, the electrical contact surfaces 400 may be generally planar surfaces of the side surface 334a of the core base portion 328 that are coated or plated with an electrically conductive material such as gold, nickel, platinum, electrolytic nickel and gold, etc., where such coating is provided via electroplating, photo deposition, vapor deposition, etc. In one embodiment, the conductive material forming the surfaces 400 shall be in the form of a plating having a minimum thickness of 75 micro inches.

The electrical insulation surfaces 402 may be generally planar surfaces of the side surface 334a of the core base portion 328 that are free from any electrically conductive coating. Because of the electrical insulation surfaces 402, 360a, 360b, and 360c, the electrical contact surfaces 400 are electrically isolated from each other and the adjacent electrically conductive portions of the surfaces 295, 300, 360a, and 360b of the core lower portion 328.

Figure 10C:
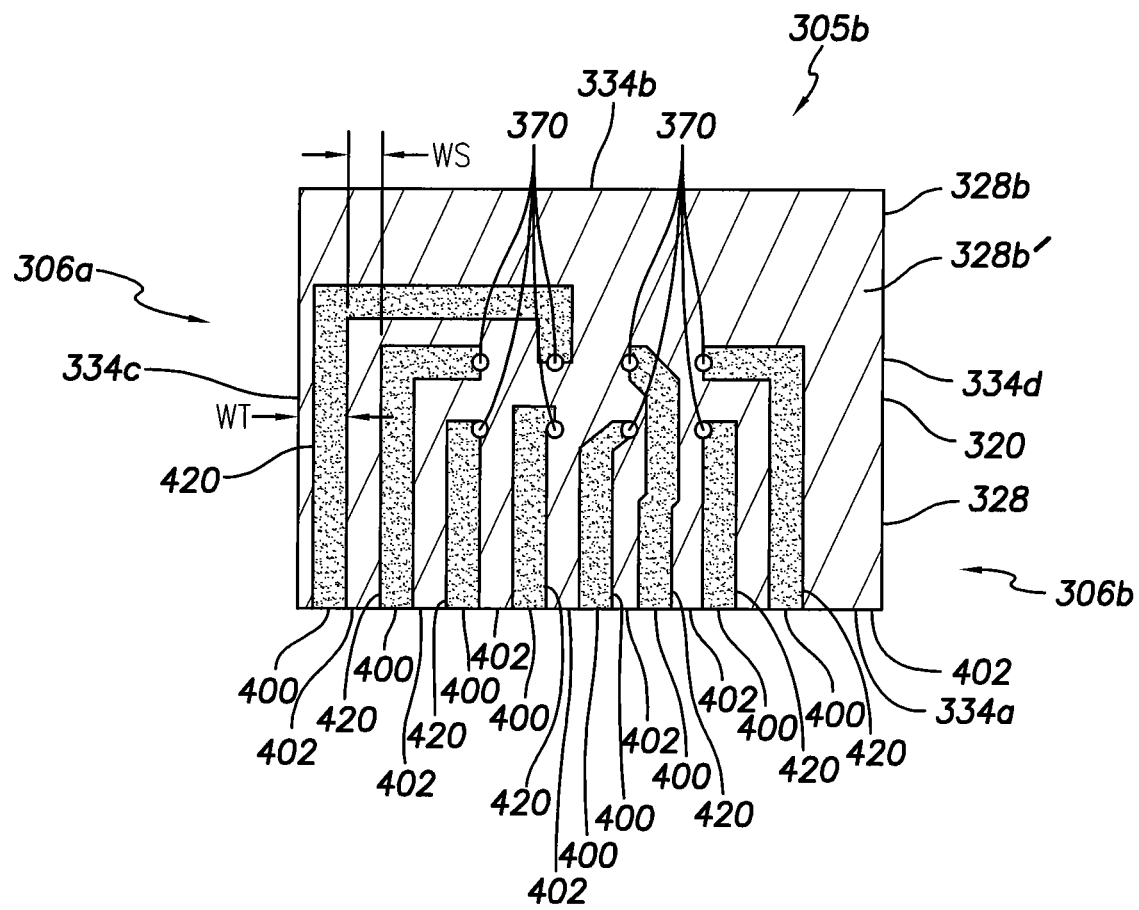
FIG. 10C is a cross-section plan view of the feeder traces extending through the core as taken along section line 10C-10C in FIGS. 9D and 10B.

As indicated in FIG. 10C, which is a cross-section plan view of feeder traces 420 extending through the core 320 as taken along section line 10C-10C in FIGS. 9D and 10B, feeder traces 420 may electrically connect the electrical contact surfaces 400 with the vias 370. Thus, the electrical contact surfaces 400, feeder traces 420, vias 370, power traces 350, and tabs 270 may be in electrical communication with each other and the power sides 290a of the capacitor chips 290, thereby forming a power side circuit of the feedthru 55.

Figure 11:
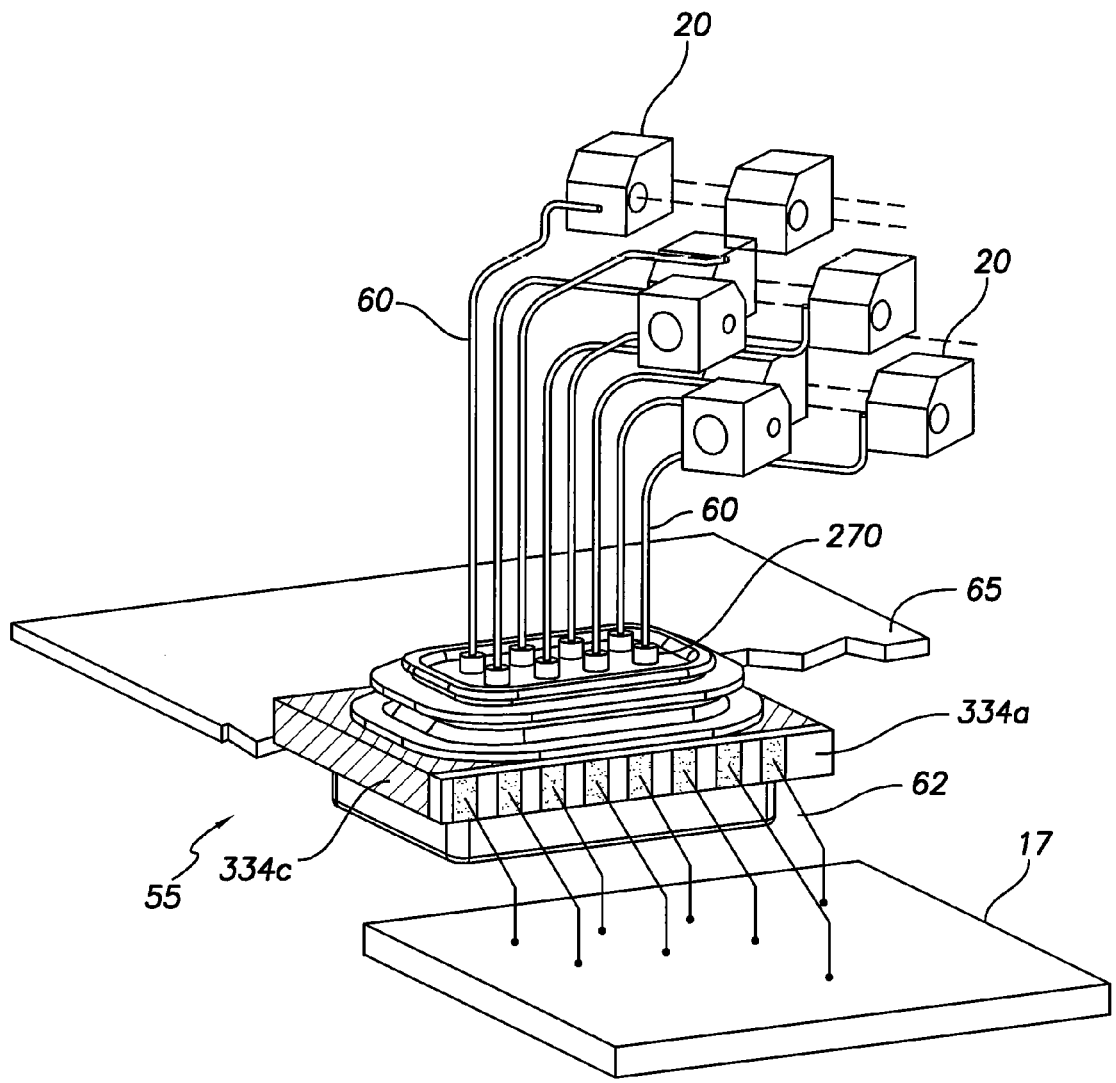
FIG. 11 is an isometric view of the feedthru of FIG. 8A mounted in the can wall of an implantable pulse generator.

As indicated in FIG. 11, which is an isometric view of the feedthru 55 of FIG. 8A mounted in the can wall 65 of an implantable pulse generator, when the feedthru 55 is installed in the pulse generator, the pulse generator's electronic components 17 (e.g., output flex, hybrid, or various other electronic components) housed within the can 15 may be electrically connected to the electrical contact surfaces 400 via conductors 62 (e.g., round wires, flat ribbon wires, flex cables, wire bond, or etc.) extending between the electrical contact surfaces 400 and the electronic components 17. Similarly, conductors 60 (e.g., round wires, flat ribbon wires, flex cables or etc.) may extend from the tabs 270 to the respective connector blocks 20 within the header of the pulse generator. Thus, the power circuit (e.g., the electrical contact surfaces 400, feeder traces 420, vias 370, power traces 350, and tabs 270) and conductors 60, 62 place the electronic components 17 in electrical communication with the connector blocks 20 and the power sides 290a of the chip capacitors 290. The ground circuit (e.g., the conductive surfaces 334b-334d and 333 of the core 320, and the feedthru housing 315) place the ground sides 290b of the chip capacitors 290 in electrical communication with the wall 65 of the can 15 of the pulse generator 5.

As shown in FIGS. 10B and 10C, one or more feeder traces 420 may extend through the core lower portion 328. The feeder traces 420 are spaced apart from each other and physically and electrically isolated from each other by the material of the core lower portion 328 that exists between the adjacent feeder traces 420.

As can be understood from FIG. 10B, in one embodiment, the core lower portion 328 may have a top section 328a (i.e., the section 328a of the core lower portion 328 located above section line 10C-10C in FIG. 10B) and a bottom section 328b (i.e., the section 328b of the core lower portion 328 located below section line 10C-10C in FIG. 10B) that are joined together via brazing, epoxy, etc. in a sandwich fashion to form a joined unitary piece core lower portion 328.

As can be understood from FIGS. 10B and 10C, in one embodiment, the feeder traces 420 may extend across an upper surface 328b' of the bottom section 328b of the core lower portion 328. Specifically, the feeder traces 420 may be formed of an electrically conductive material such as gold, nickel, platinum, electrolytic nickel and gold, etc., where such coating is provided on the upper surface 328' of the bottom section 328b of the core lower portion 328 via electroplating, photo deposition, vapor deposition, etc. In one embodiment, the conductive material shall be in the form of a plating having a minimum thickness of 75 micro inches. When being deposited on the upper surface 328b', the feeder traces 420 may be caused to be routed between locations corresponding to respective vias 370 and respective side contacts 400.

Once the feeder traces 420 are deposited on the upper surface 328b' of the bottom section 328b of the core lower portion 328 as shown in FIG. 10C, the bottom section 328b is joined to the top section 328a in the above-described sandwich fashion by abutting the upper surface 328b' of the bottom section 328b to the lower surface of the top section 328a, the feeder traces 420 being sandwiched between the top section 328a and bottom section 328b as shown in FIG. 10B.

In other embodiments, the feeder traces 420 are deposited on the lower surface of the top section 328a of the core lower portion 328, and then the lower surface of the top section 328a and the upper surface 328b' of the top section 328b are abutted together to sandwich together the top section 328a and bottom section 328b. In yet other embodiments, the feeder traces 420 are deposited on an electrically insulating substrate, which is then sandwiched between the top section 328a and the bottom section 328b.

While the feeder traces 420 are discussed above as being in the form of traces deposited on the surface of a section of the core lower portion 328 via electroplating, photo deposition, vapor deposition, etc., in other embodiments, the feeder traces 420 may be in the form of other electrical conductor configurations. For example, in some embodiments, the feeder traces 420 may be in the form of electrically conductive wires, cable, etc. that are imbedded in the core lower portion 328 during the process of molding the core lower portion 328.

In one embodiment, as can be understood from FIG. 10B, the feeder traces 420 may be imbedded in the core lower portion 328 in a plane that is approximately 0.006 inch above the can face 335 and on a level approximately equal to that depicted by section line 10C-10C in FIG. 10B.

As can be understood from FIG. 10C, in one embodiment, an individual feeder trace 420 may have a width WT of approximately 0.03 inch and be space apart from adjacent feeder traces 420 by a width WS of approximately 0.03 inch.

As can be understood from FIGS. 1 and 8A-11, in one embodiment, an implantable pulse generator 5 may include a header 25, a can 15, and a feedthru 55. The header may include a lead connector block 20 electrically coupled to a first conductor 60. The can 15 may be coupled to the header 25 and include a wall 65 and an electronic component 17 electrically connected to a second conductor 62 and housed within the wall 65. The feedthru 55 may be mounted in the wall 65 and include a header side 295, a can side 300, an electrical insulating core 320, a ground circuit, and a power circuit. The core 320 may include a first surface 330 forming at least part of the header side 295, a second surface 335 forming at least part of the can side 300, and a third surface 334a lateral to at least one of the first surface 330 and second surface 335.

As can be understood from FIGS. 10B, 10C and 11, the power circuit may extend through the core 320 from the third surface 334a to the first surface 330. The first conductor 60 may be electrically connected to the power circuit near the first surface 330, and the second conductor 62 may be electrically connected to the power circuit near the third surface 334a. As can be understood from FIGS. 8C, 8D and 11, at least a portion of the ground circuit may extend along the second surface 335 and is electrically coupled to the wall 65.

As indicated in FIGS. 10B and 10C, the power circuit may include a first portion 370 extending through the core 320 between the first surface 330 and the second surface 335. The power circuit may further include a second portion 420 extending generally laterally through the core 320 from the third surface 334a to the first portion 330.

As indicated in FIG. 8C, the feedthru 55 may also include a chip capacitor 290. The second surface 335 may include an electrically conductive layer 350 electrically connected to a portion 370 of the power circuit and spaced apart from the at least a portion (represented by cross-hatching) of the ground circuit extending along the second surface 335. The chip capacitor 290 may electrically span between the electrically conductive layer 350 and the at least a portion (represented by cross-hatching) of the ground circuit extending along the second surface 335.

Figure 12A:
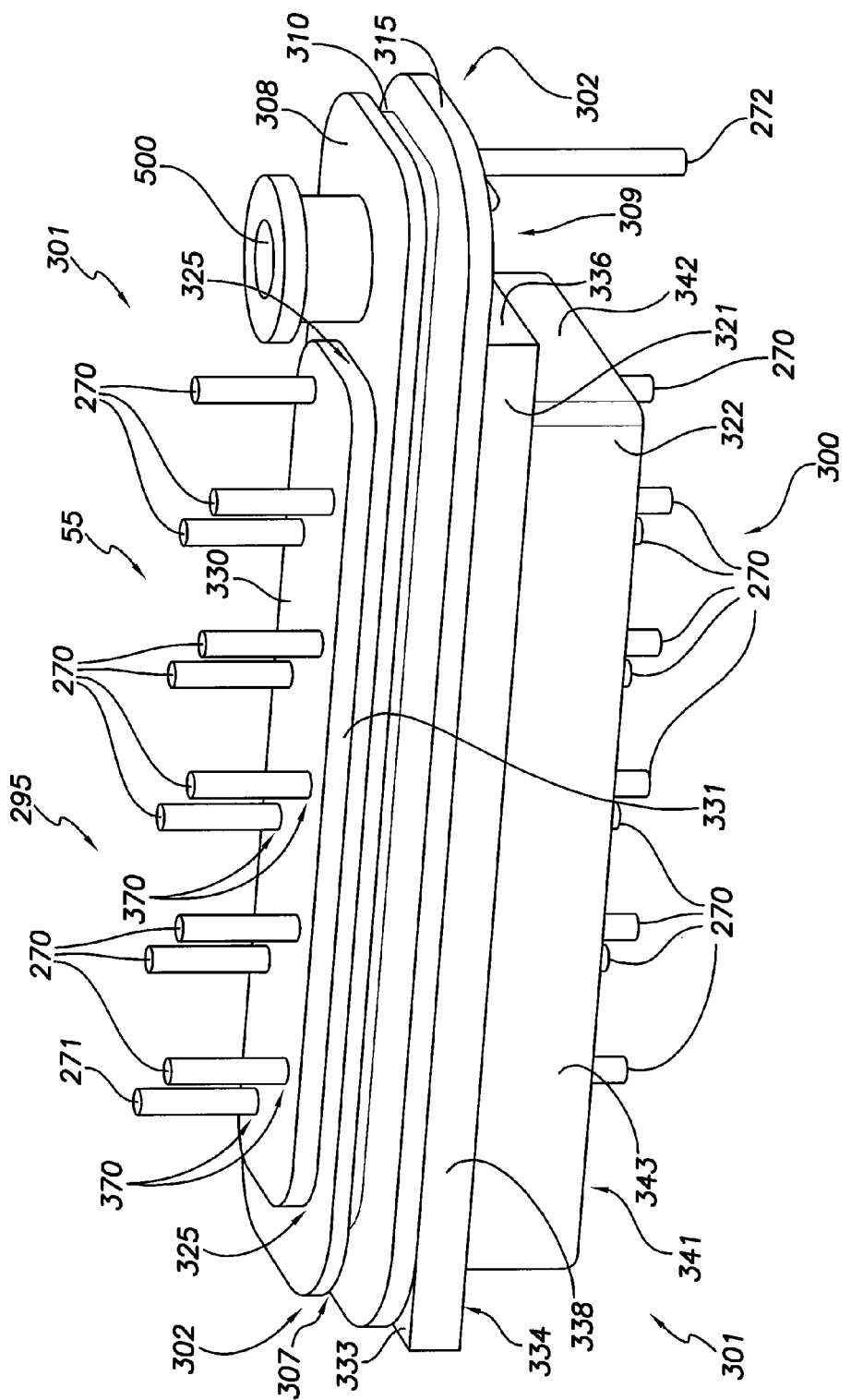
FIG. 12A is a side-top isometric view of another embodiment of the feedthru.
Figure 12B:
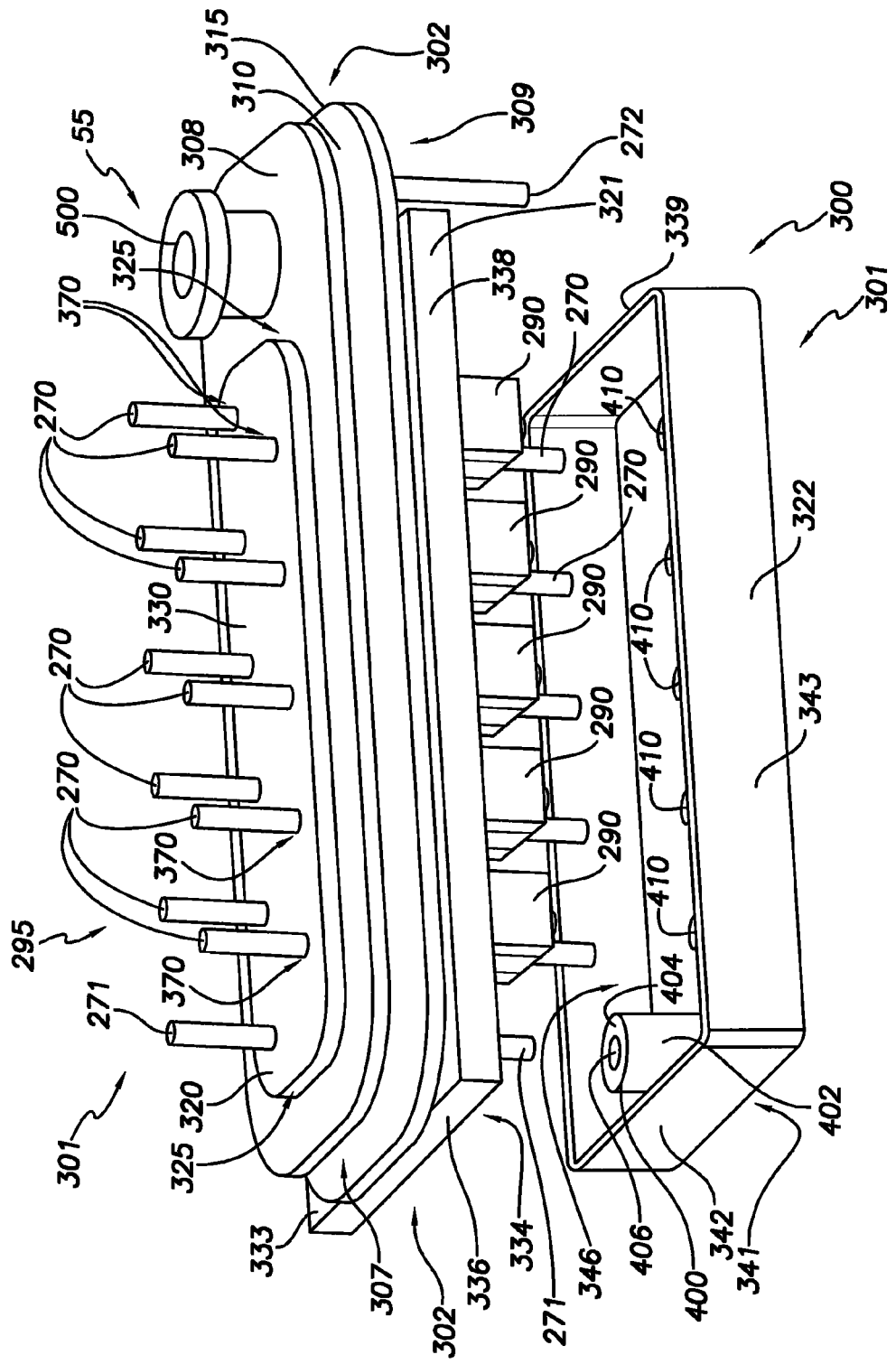
FIG. 12B is another side-top isometric view of the feedthru of FIG. 12A, wherein the feedthru is in a partially exploded state with the shield separated from the rest of the feedthru.
Figure 13A:
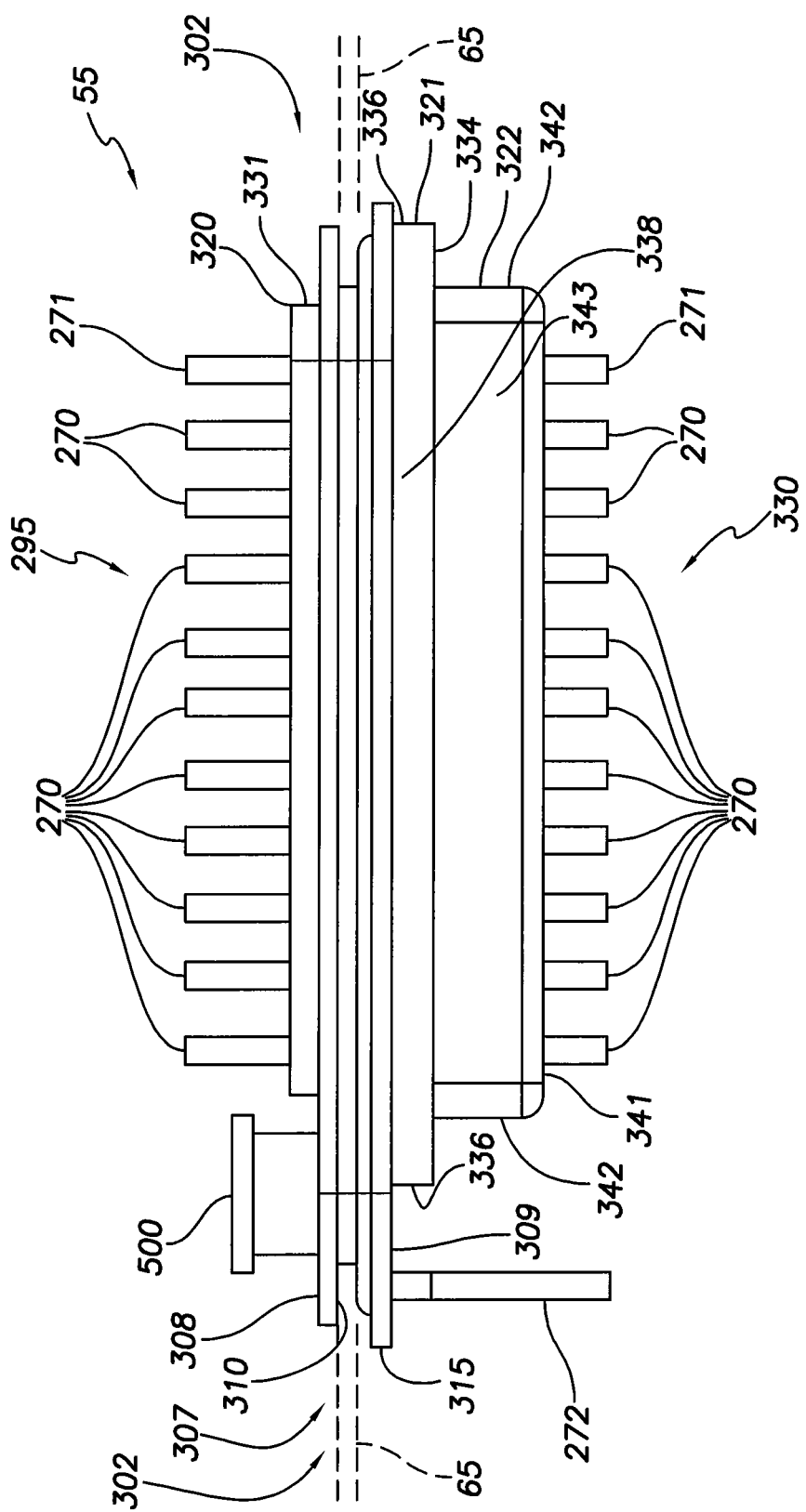
FIG. 13A is a side elevation view of the feedthru.
Figure 13B:
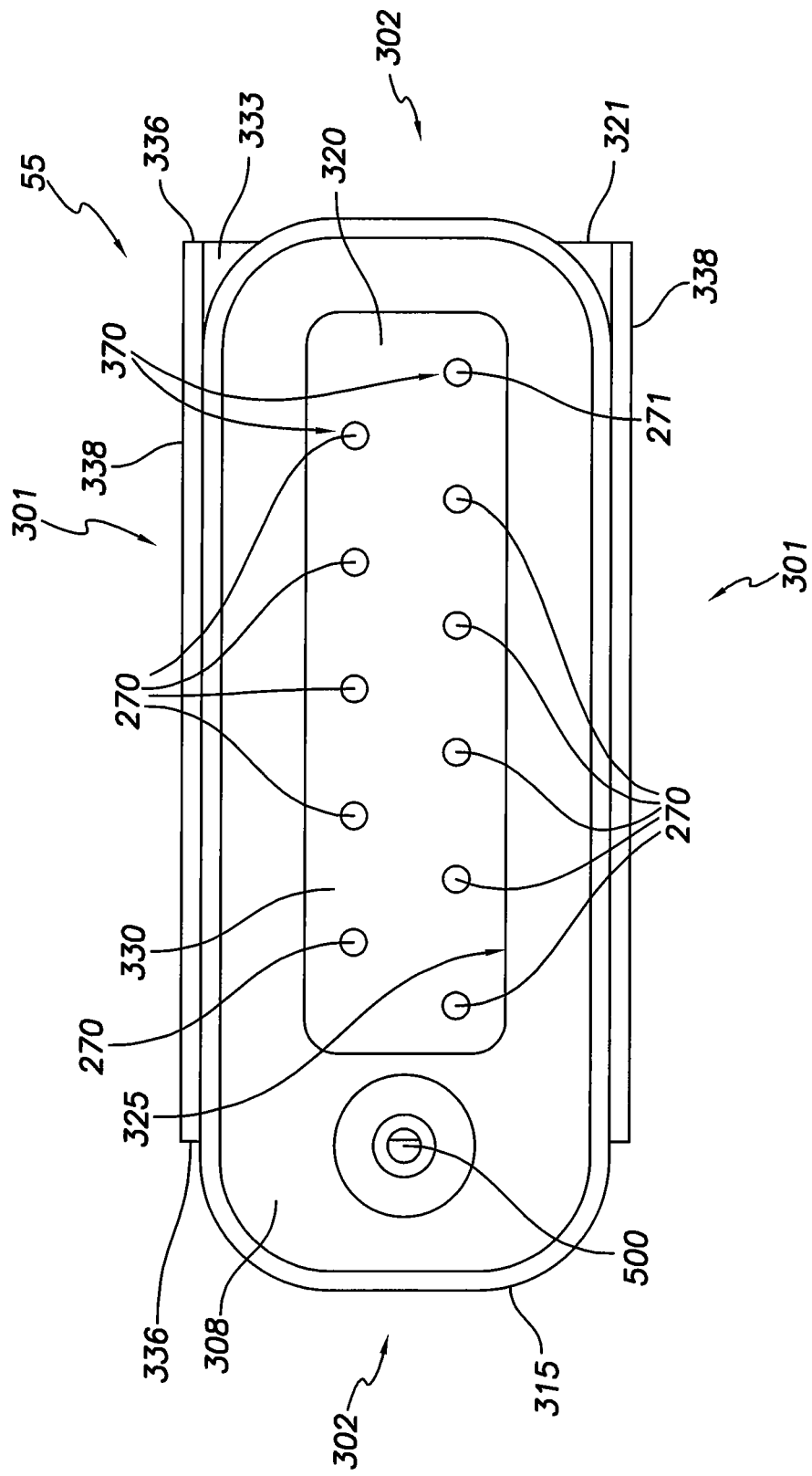
FIG. 13B is a top plan view of the feedthru.
Figure 13C:
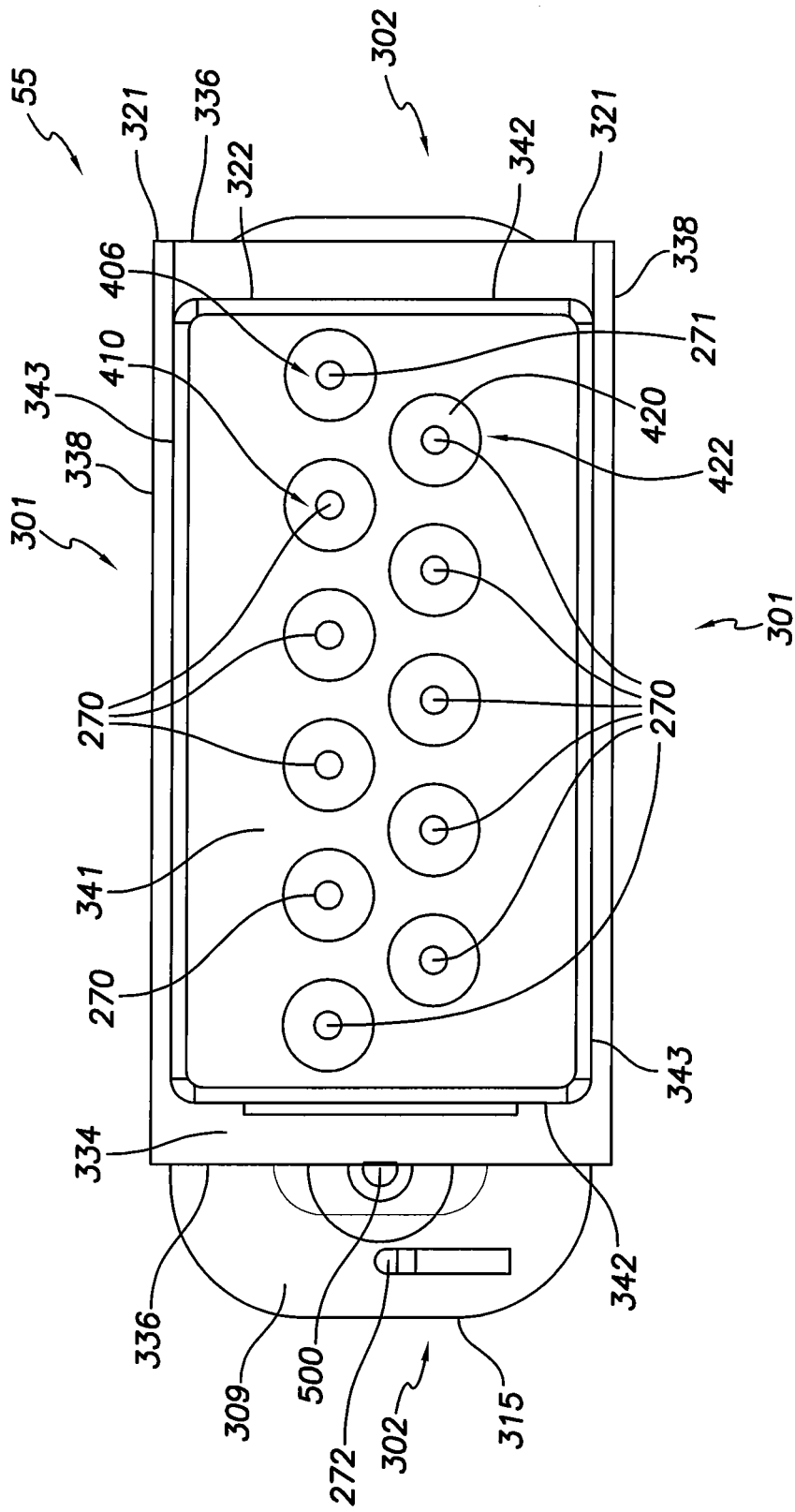
FIG. 13C is a bottom plan view of the feedthru.

To begin a detailed discussion regarding yet another embodiment of a feedthru 55 that may be employed with a pulse generator 5 similar to that depicted in FIG. 1, reference is now made to FIGS. 12A-13C. FIG. 12A is a side-top isometric view of the feedthru 55. FIG. 12B is another side-top isometric view of the feedthru 55 in a partially exploded state with the shield 322 separated from the rest of the feedthru 55. FIGS. 13A-13C are, respectively, a side elevation, a top plan view and a bottom plan view of the feedthru 55.

In one embodiment, as shown in FIGS. 12A-13A, the feedthru 55 includes a header side 295, a can side 300, and sides 301 and ends 302. As can be understood from FIGS. 12A-12B and 13B-13C, the overall configuration of the feedthru 55 may be generally rectangular in some embodiments. However, in other embodiments, similar to as discussed above with respect to the preceding embodiments, the feedthru 55 may have other configurations.

As illustrated in FIGS. 12A-13C, in one embodiment, the feedthru 55 includes a feedthru housing 315, a core 320, a substrate or printed circuit board ("PCB") 321, a shield 322, chip capacitors 290, feedthru tabs, pins, posts or wires 270, a RF tab, pin, post or wire 271, a ground tab, pin, post or wire 272 and ground and power circuits. The housing 315 has an outer contoured side 307, a header face 308, a can face 309, and a central or core-receiving opening 325. The contoured side 307 of the housing 315 includes the groove or slot 310 that receives the can wall 65 when the feedthru is mounted in the can wall. The central opening 325 of the housing 315 extends axially through the housing and defines a void that is occupied by the core 320. When the housing 315 is mounted in the can wall 65, the header face 308 faces the header, and the can face 309 faces towards the interior of the can. The housing 315 may be machined, molded or otherwise formed to fit the space and design constraints of an implantable pulse generator 5. The housing 315 may be titanium, a titanium alloy, MP35N, or stainless steel.

As can be understood from FIG. 12A-13B, in one embodiment, the core 320 includes a header face 330, sides 331, and a can face. The can face of the core 320 is similar to the can face 335 of the core of FIG. 10B and abuts against the printed circuit board ("PCB") 321. The core sides 331 extend generally perpendicularly between the core header face 330 and the core can face. The core sides 331 are configured such that the core 320 may be matingly received in the core-receiving opening 325 of the housing 315. When the core 320 is received in the core-receiving opening 325, the core can face and housing can face 309 may be generally flush with each other and both abut against a header face 333 of the PCB 321. The core 320 may be formed of an electrically insulating material, such as ceramic, glass, sapphire, ceramic 99% minimum pure alumina, or etc.

The core 320 includes vias or through-holes 370 extending axially there through. In one embodiment, the electrically conductive elements 270, 271, extend as wires, pins or posts in a continuous, uninterrupted manner through the through-holes 370 extending through the core 320 and PCB 321. As can be understood from FIG. 1, the header ends of the wires, pins or posts 270, 271 are coupled to the conductors 60 extending to the elements 20 in the header 25. Similarly, the can ends of the wires, pins or posts 270, 271 are coupled to the conductors 62 extending to the elements 17 in the can 15. In other embodiments, the electrically conductive elements 270, 271 are tabs or similarly configurations as discussed above with respect to FIGS. 6A-7H.

In one embodiment, the vias 370 may be as discussed above with respect to FIG. 10B. Specifically, the vias 370 may be in the form of electrically conductive through-holes 370 lined with electrically conductive coatings 243. In such embodiments, the surfaces of the through-holes 370 may be coated with an electrically conductive material 243 (FIG. 10B), such as gold, nickel, platinum, etc., where such coating is provided via electroplating, photo deposition, vapor deposition, etc. In other embodiments, the vias 370 are not lined with an electrically conductive material.

Figure 14A:
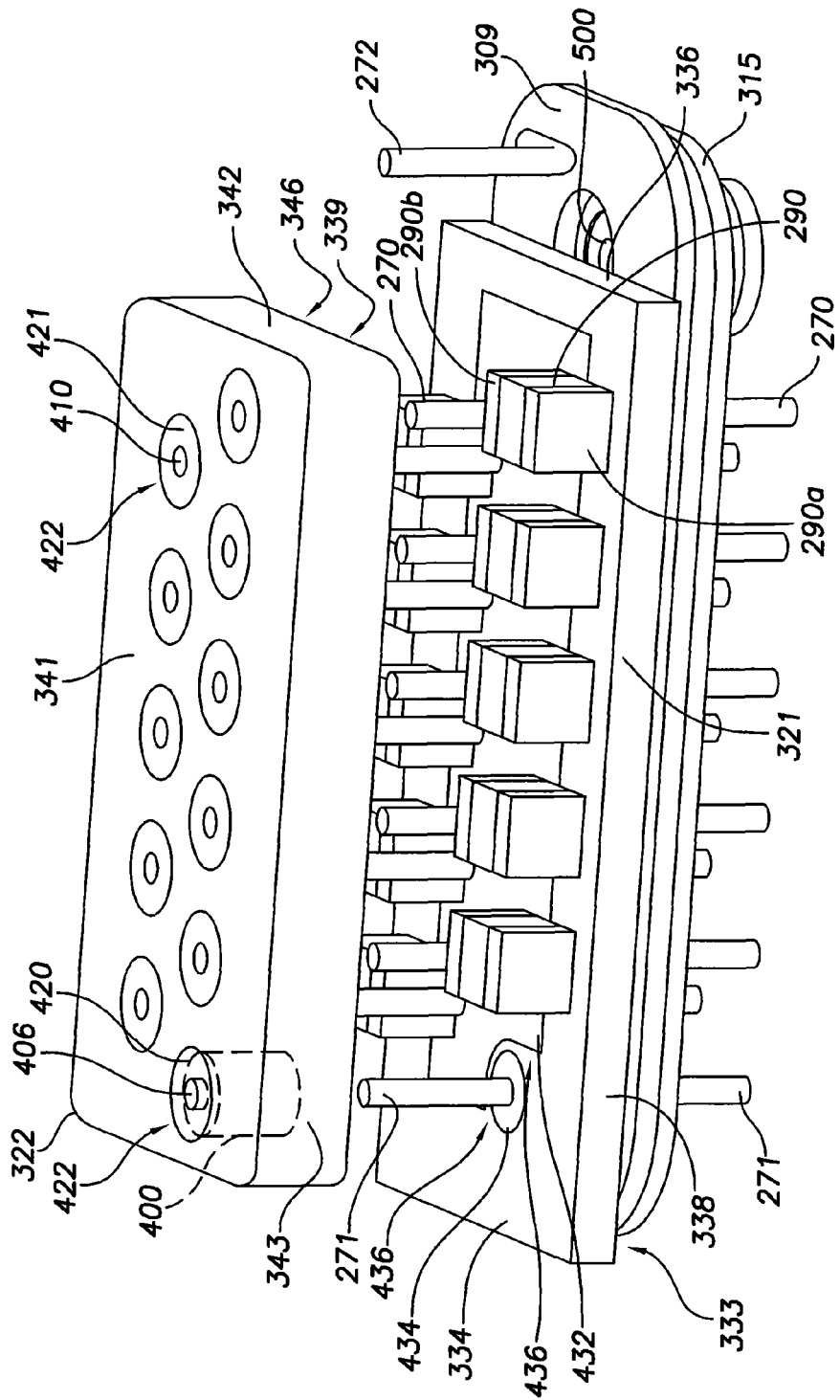
FIG. 14A is a bottom-side isometric view of the feedthru with the shield removed from the can face of the PCB.
Figure 14B:
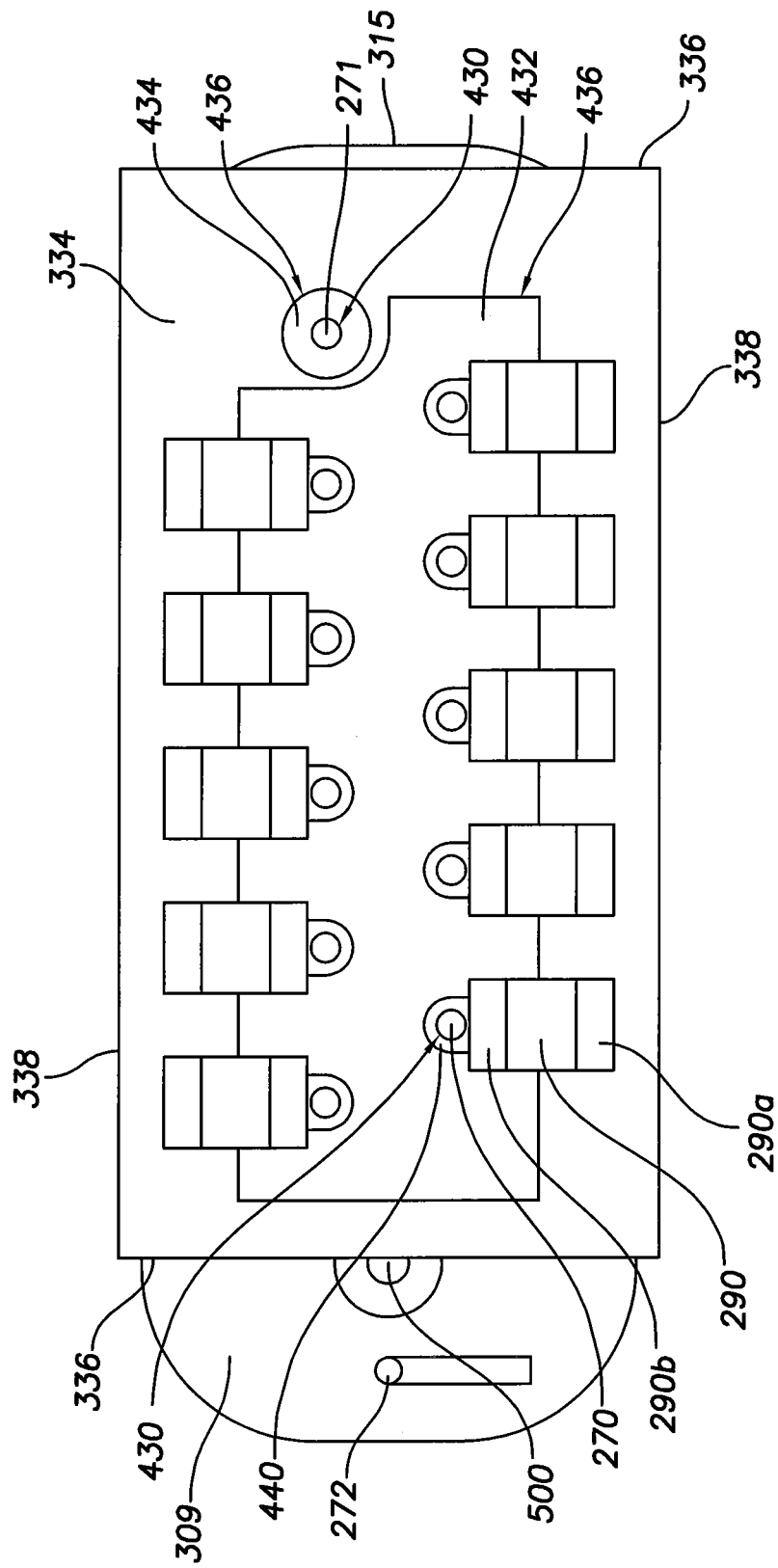
FIG. 14B is a bottom plan view of the feedthru with the shield removed from the can face of the PCB.

As indicated in FIGS. 12A-13B and further indicated in FIGS. 14A and 14B, which are, respectively, a bottom-side isometric and a bottom plan view of the feedthru 55 with the shield 322 removed from the can face 334 of the PCB 321, the PCB 321 includes a header face 333, a can face 334, end faces 336, and side faces 338. The shield 322 includes a header edge 339, a can face 341, end faces 342, side faces 343, and a hollow interior 346 defined by the walls forming the various faces 341, 342, 343.

As illustrated in FIG. 12B, a cylindrical member 400 extends generally perpendicularly from the interior side of the wall of the shield 322 that forms the can face 341 of the shield 322. The cylindrical member 400 includes a cylindrical outer surface 402, a header face 404 on a free end of the member 400 generally opposite the intersection of the cylindrical member 400 with the wall forming the shield can face 341, and a hole 406 extending generally longitudinally axially through the cylindrical member 400 and wall forming the can face 341 of the shield.

As depicted in FIGS. 12B and 14A, holes 410 extend through the wall of the shield 322 that forms the can face 341 of the shield 322. Such holes 410 have the same spacing pattern as the wires or pins 270.

When the feedthru 55 is fully assembled, as depicted in FIGS. 12A and 13A-13C, the core 320 is received in the housing 315, the PCB header face 333 abuts against the housing can face 309 and the core can face, the header edge 339 of the shield 322 abuts against the PCB can face 334, the chips 290 are coupled to the PCB can face 334 and received in the hollow interior 346 such that the shield 322 and PCB can face 334 fully enclose or encase the chips 290, the wires 270 extend through the corresponding holes 410, and the RF wire 271 extends through the hole 406 of the cylindrical member 400.

In one embodiment, the walls of the shield 322 are formed of an electrically non-conductive material such as a polymer, ceramic, etc. As can be understood from FIGS. 12A-12B, 13C and 14A, in one embodiment, the entirety of the exterior surfaces (i.e., the can face 341, the end faces 342, and the side faces 343) of the shield 322 are metalized (e.g., coated or otherwise provided with an electrically conductive surface), except in electrically non-conductive regions 420 surrounding the holes 406, 410. As indicated in FIG. 13C, the electrically non-conductive regions 420, which may be defined in the metalized surfaces via, for example, a circular or other shaped boarder 422, electrically isolate the wires 270, 271 extending out of the can face 341 of the shield 322 from the metalized surface of the shield can face 341. In some embodiments, the interior surfaces of the holes 406, 410 are metalized, as long as the metalized surfaces of the holes 406, 410 are not electrically connected to the metalized surfaces of the shield 322.

As can be understood from FIGS. 12A-12B, 13C and 14A, in one embodiment, the entirety of the header edge 339 of the shield 322 and entirety of the surfaces of the interior 346 of the shield 322 are electrically non-conductive (i.e., free of a metalized layer or coating), except the cylindrical outer surface 402 of the cylindrical member 400, the cylindrical outer surface 402 being metalized as discussed above with respect to the exterior surfaces of the shield 322. The metalized cylindrical outer surface 402 and the metalized cylindrical inner surface of the hole 406 extending axially through the cylindrical member 400 may act as a shield for the RF wire 271, which extends through the hole 406 and is not electrically coupled to a chip 290. The free end surface 404 of the cylindrical member 400 is also electrically non-conductive (i.e., free of a metalized layer or coating). In some embodiments, the entirety of the header edge 339 of the shield 322 is metalized.

In one embodiment, the PCB 321 is formed of an electrically non-conductive material such as a polymer, ceramic, etc. As can be understood from FIGS. 12A-12B and 14A-14B, in one embodiment, the entirety of the exterior surfaces (i.e., the header face 333, the can face 334, the end faces 336, and the side faces 338) of the PCB 321 are metalized (e.g., coated or otherwise provided with an electrically conductive surface), except in electrically non-conductive regions surrounding the holes 430 in the PCB 321 through which the wires 270, 271 extend through the PCB 321. For example, as indicated in FIG. 14B and with respect to the PCB can face 334, electrically non-conductive regions 432, 434, which may be defined in the metalized surface of the PCB can face 334 via, for example, circular, rectangular or other shaped boarders 436, electrically isolate the wires 270, 271 extending out of the can face 334 of the PCB 321 from the metalized surface of the PCB can face 334. In some embodiments, the interior surfaces of the holes 430 are metalized.

Although not illustrated in any view, in some embodiments, the header face 333 of the PCB 321 has an arrangement of metalized and non-electrically conductive surfaces that is generally identical to what is described above with respect to the PCB can face 334 of FIG. 14B. As a result, the electrically non-conductive regions of the PCB header face 333 electrically isolate the wires 270, 271 extending into of the header face 333 of the PCB 321 from the metalized surface of the PCB header face 333.

As illustrated in FIG. 14B, traces 440 are located on the electrically non-conductive region 432 of the PCB can face 334, surrounding the each of the holes 430 though which the wires 270 extend out of the PCB can face 334. The traces 440 may be electrically connected to the metalized inner surface of the holes 430, where such metalized inner surfaces are present.

As depicted in FIGS. 14A and 14B, each chip 290 includes a negative or ground contact side 290a and a positive or power contact side 290b. Each chip 290 extends across a portion of the electrically non-conductive region 432 separating the metalized surface of the PCB can side 334 from the traces 440. The ground side 290a of each chip 290 electrically contacts the metalized surface of the PCB can side 334, and the power side 290b of each chip 290 electrically contacts the chip's respective trace 440.

As can be understood from FIGS. 1 and 12A-14B and the preceding discussion, the metalized portions of the PCB header face 333 are in electrical contact with the feedthru housing 315 via the PCB header face 333 abutting against the housing 315 when the feedthru 55 is fully assembled. Accordingly, a ground circuit extends from the ground side 290a of each chip 290, to the metalized portions of the PCB can face 334, to the metalized PCB end and side faces 336, 338, to the metalized portions of the PCB header face 333, to the feedthru housing 315 and, finally, into the can housing 65. The ground circuit also may include the wire 272, which is welded to the housing 315 and may extend from components within the can 15.

As can be understood from FIGS. 1 and 12A-14B and the preceding discussion, the wires 270 extend through the respective holes 370, 410, 430 in the core 320, PCB 321 and shield 322 from the conductors 62 coupled to the components in the can 15 to the conductors 60 leading to the elements in the header 25, and each of these wires 270 is electrically coupled to a power side 290b of a respective chip 290 via a respective trace 440. Thus, a power circuit extends along the wires 270 through the feedthru 55 and is electrically coupled to the chips via the traces 440 leading into the power sides 290b of the chips 290. Thus, the chips 290 and filter the power circuit.

As can be understood from FIGS. 1 and 12A-14B and the preceding discussion, the RF wire 271 extends through the holes in the core 320, PCB 321 and shield 322 from a respective conductor 62 coupled to the RF components in the can 15 to the conductors 60 leading to the RF antenna in the header 25. The resulting RF circuit is shielded by the metalized surfaces 402 of the cylindrical member 400. The metalized exterior surfaces of the shield 322 and PCB 321 also serve to shield the RF circuit and portions of the power circuit extending through these portions of the feedthru 55.

As indicated in FIGS. 12A-14B, a fill port 500 opens through the feedthru housing 315. Once the housing 315 is welded into the can wall 65, the fill port 500 may be employed to fill the volume of the can 15 with nitrogen, which is a good dielectric. The fill port 500 can then be plugged with a titanium ball and welded shut to maintain the nitrogen within the volume of the can 15.

Although the present invention has been described with reference to preferred embodiments, persons skilled in the art will recognize that changes may be made in form and detail without departing from the spirit and scope of the invention.

What is claimed is:

1. An implantable pulse generator comprising:
    a header including a lead connector block electrically coupled to a first conductor;
    a can coupled to the header and including a wall and an electronic component electrically coupled to a second conductor and housed within the wall; and
    a feedthru mounted in the wall and including a header side, a can side, an electrical insulating core, a printed circuit board (PCB), a chip capacitor, a ground circuit, and a power circuit;
    wherein the core includes a first surface and a second surface, the first surface of the core forming at least part of the header side;
    wherein the PCB includes a first surface and a second surface, the first surface of the PCB abutting against the second surface of the core, the second surface of the PCB forming at least part of the can side and including a first electrically conductive region, a second electrically conductive region, and a first electrically non-conductive region separating the first electrically conductive region from the second electrically conductive region;
    wherein the power circuit extends through the PCB and core from the second conductor to the first conductor and is electrically connected to the second electrically conductive region;
    wherein the chip capacitor includes a first electrical contact electrically connected to the first electrically conductive region and a second electrical contact electrically connected to the second electrically conductive region, the chip capacitor spanning across the first electrically non-conductive region;
    wherein at least a portion of the ground circuit extends along the first electrically conductive region and is electrically coupled to the wall;
    wherein the second surface of the PCB further includes a second electrically non-conductive region surrounded by portions of the first electrically conductive region;
    wherein the feedthru further includes a radio frequency (RF) circuit extending through the second electrically non-conductive region as the RF circuit extends through the PCB and core;
    wherein the feedthru further includes a shield abutting against the second surface of the PCB and enclosing the chip capacitor; and
    wherein the shield includes a member having a metalized surface, the RF circuit extending through the member.

2. The pulse generator of claim 1, wherein the feedthru further includes a housing in which the core is received and to which the wall is welded, the PCB further including a third surface having a third electrically conductive region electrically coupled to the first electrically conductive region and the housing.

3. The pulse generator of claim 1, wherein the second electrically conductive region includes a trace.

4. The pulse generator of claim 1, wherein the first electrically conductive region includes a metalized layer on the second surface of the PCB.

5. The pulse generator of claim 1, wherein the power circuit through the PCB and core includes a generally continuous wire.

6. An implantable pulse generator comprising:
a header including a lead connector block electrically coupled to a first conductor;
a can coupled to the header and including a wall and an electronic component electrically coupled to a second conductor and housed within the wall; and
a feedthru mounted in the wall and including a header side, a can side, an electrical insulating core, a printed circuit board (PCB), a chip capacitor, a ground circuit, and a power circuit;
wherein the core includes a first surface and a second surface, the first surface of the core forming at least part of the header side;
wherein the PCB includes a first surface and a second surface, the first surface of the PCB abutting against the second surface of the core, the second surface of the PCB forming at least part of the can side and including a first electrically conductive region, a second electrically conductive region, and a first electrically non-conductive region separating the first electrically conductive region from the second electrically conductive region;
wherein the power circuit extends through the PCB and core from the second conductor to the first conductor and is electrically connected to the second electrically conductive region;
wherein the chip capacitor includes a first electrical contact electrically connected to the first electrically conductive region and a second electrical contact electrically connected to the second electrically conductive region, the chip capacitor spanning across the first electrically non-conductive region;
wherein at least a portion of the ground circuit extends along the first electrically conductive region and is electrically coupled to the wall;
wherein the second surface of the PCB further includes a second electrically non-conductive region surrounded by portions of the first electrically conductive region;
wherein the feedthru further includes a radio frequency (RF) circuit extending through the second electrically non-conductive region as the RF circuit extends through the PCB and core;
wherein the feedthru further includes a shield abutting against the second surface of the PCB and enclosing the chip capacitor; and
wherein the shield includes a metalized exterior surface electrically coupled to the first electrically conductive region.

7. The pulse generator of claim 6, wherein the first and second surfaces of the core and the first and second surfaces of the PCB are generally parallel to each other.

8. The pulse generator of claim 6, wherein the core is formed of a ceramic material.

9. The pulse generator of claim 6, wherein at least one of the first conductor or second conductor is at least one of round wire, flat ribbon wire, flex cable, or wire bond.

10. An implantable pulse generator comprising:
a header including a lead connector block electrically coupled to a first conductor;
a can coupled to the header and including a wall and an electronic component electrically connected to a second conductor and housed within the wall; and
a feedthru mounted in the wall and including an electrically insulating core, a printed circuit board (PCB), a shield, a chip capacitor, a power circuit and a ground circuit;
wherein a first side of the PCB abuts against the core and a second side of the PCB abuts against an edge of the shield, the chip capacitor mounted on the second side of the PCB, the chip capacitor being enclosed in a volume defined by an interior of the shield and the second side of the PCB;
wherein a first electrical contact of the chip capacitor is electrically coupled to the power circuit, which extends between the first and second conductors;
wherein a second electrical contact of the chip capacitor is electrically coupled to the ground circuit, which is electrically coupled to the wall;
wherein portions of the ground circuit include a metalized surface of the PCB; and
wherein portions of the ground circuit further include a metalized exterior surface of the shield, the metalized exterior surface of the shield electrically coupled to the metalized surface of the PCB.

11. The pulse generator of claim 10, wherein the first electrical contact of the chip capacitor is electrically coupled to the power circuit via a trace on PCB, the second electrical contact of the chip capacitor is electrically coupled to the ground circuit via the metalized surface of the PCB, the trace is separated from the metalized surface of the PCB via an electrically non-conductive portion of the PCB, and the chip capacitor extends across the electrically non-conductive portion of the PCB.

12. The pulse generator of claim 10, wherein the feedthru further includes a radiofrequency (RF) circuit, the shield further including a portion extending through the volume, the portion including a metalized exterior surface, the RF circuit extending through the portion.

13. The pulse generator of claim 12, wherein at least the power circuit or RF circuit through the feedthru includes a continuous wire.

* * * * *